(12) United States Patent
Kennedy et al.

(10) Patent No.: US 10,994,040 B2
(45) Date of Patent: May 4, 2021

(54) SURFACE TREATMENT WITH ULTRAVIOLET LIGHT

(71) Applicant: Sensor Electronic Technology, Inc., Columbia, SC (US)

(72) Inventors: Robert M. Kennedy, Columbia, SC (US); Faris Mills Morrison Estes, Columbia, SC (US); Alexander Dobrinsky, Silver Spring, MD (US)

(73) Assignee: Sensor Electronic Technology, Inc., Columbia, SC (US)

( * ) Notice: Subject to any disclaimer, the term of this patent is extended or adjusted under 35 U.S.C. 154(b) by 92 days.

(21) Appl. No.: 15/989,261

(22) Filed: May 25, 2018

(65) Prior Publication Data

US 2018/0339075 A1  Nov. 29, 2018

Related U.S. Application Data

(60) Provisional application No. 62/511,666, filed on May 26, 2017.

(51) Int. Cl.
| | |
|---|---|
| *A61L 2/24* | (2006.01) |
| *A61L 2/10* | (2006.01) |
| *E05B 1/00* | (2006.01) |
| *G07F 19/00* | (2006.01) |
| *B67D 7/42* | (2010.01) |

(52) U.S. Cl.
CPC .................... *A61L 2/24* (2013.01); *A61L 2/10* (2013.01); *E05B 1/0069* (2013.01); *A61L 2202/11* (2013.01); *A61L 2202/121* (2013.01); *A61L 2202/14* (2013.01); *A61L 2202/20* (2013.01); *B67D 7/42* (2013.01); *G07F 19/201* (2013.01)

(58) Field of Classification Search
CPC .......... A61L 2/24; A61L 2/10; A61L 2202/11; A61L 2202/14; A61L 2202/20; A61L 2202/121; G07F 19/201; B67D 7/42; E05B 1/0069
USPC ...................................................... 250/455.11
See application file for complete search history.

(56) References Cited

U.S. PATENT DOCUMENTS

| | | | |
|---|---|---|---|
| 4,710,634 A | * | 12/1987 | Brookes .................... A61L 2/10 250/455.11 |
| 7,553,456 B2 | | 6/2009 | Gaska et al. |
| 7,634,996 B2 | | 12/2009 | Gaska et al. |
| 8,277,734 B2 | | 10/2012 | Koudymov et al. |
| 8,980,178 B2 | | 3/2015 | Gaska et al. |
| 9,006,680 B2 | | 4/2015 | Bettles et al. |
| 9,034,271 B2 | | 5/2015 | Shur et al. |
| 9,061,082 B2 | | 6/2015 | Gaska et al. |
| 9,138,499 B2 | | 9/2015 | Bettles et al. |
| 9,179,703 B2 | | 11/2015 | Shur et al. |
| 9,572,903 B2 | | 2/2017 | Dobrinsky et al. |

(Continued)

*Primary Examiner* — Kiet T Nguyen
(74) *Attorney, Agent, or Firm* — LaBatt, LLC

(57) ABSTRACT

An approach for the treatment of surfaces in public places with ultraviolet light is disclosed. In one embodiment, a disinfection illuminator having ultraviolet radiation sources can irradiate a number of contact surfaces. A control unit can control the ultraviolet irradiation of the contact surfaces. The disinfection illuminator is suitable for a wide variety of devices that are used by the general public. Gas station pumps, door knobs, key pads, and bathrooms are illustrative of examples of some devices and places having commonly-used surfaces that can be treated by the disinfection illuminator.

20 Claims, 10 Drawing Sheets

(56) References Cited

U.S. PATENT DOCUMENTS

| | | | |
|---|---|---|---|
| 9,603,960 | B2 | 3/2017 | Dobrinsky et al. |
| 9,687,577 | B2 | 6/2017 | Dobrinsky et al. |
| 9,707,307 | B2 | 7/2017 | Shur et al. |
| 9,718,706 | B2 | 8/2017 | Smetona et al. |
| 9,724,441 | B2 | 8/2017 | Shur et al. |
| 9,750,830 | B2 | 9/2017 | Shur et al. |
| 9,757,486 | B2 | 9/2017 | Dobrinsky et al. |
| 9,795,699 | B2 | 10/2017 | Shur et al. |
| 9,801,965 | B2 | 10/2017 | Bettles et al. |
| 9,802,840 | B2 | 10/2017 | Shturm et al. |
| 10,099,944 | B2 | 10/2018 | Smetona et al. |
| 2013/0048545 | A1 | 2/2013 | Shatalov et al. |
| 2014/0060104 | A1 | 3/2014 | Shur et al. |
| 2014/0202962 | A1 | 7/2014 | Bilenko et al. |
| 2015/0165079 | A1 | 6/2015 | Shur et al. |
| 2015/0297767 | A1 | 10/2015 | Gaska et al. |
| 2015/0336810 | A1 | 11/2015 | Smetona et al. |
| 2016/0000953 | A1 | 1/2016 | Bettles et al. |
| 2016/0114186 | A1 | 4/2016 | Dobrinsky et al. |
| 2016/0324996 | A1 | 11/2016 | Bilenko et al. |
| 2017/0057842 | A1 | 3/2017 | Dobrinsky et al. |
| 2017/0100494 | A1 | 4/2017 | Dobrinsky et al. |
| 2017/0100495 | A1 | 4/2017 | Shur et al. |
| 2017/0100496 | A1 | 4/2017 | Shur et al. |
| 2017/0173200 | A1 * | 6/2017 | Wyman ................. A61L 2/24 |
| 2017/0189711 | A1 | 7/2017 | Shur et al. |
| 2017/0245527 | A1 | 8/2017 | Dobrinsky et al. |
| 2017/0245616 | A1 | 8/2017 | Lakios et al. |
| 2017/0281812 | A1 | 10/2017 | Dobrinsky et al. |
| 2017/0290934 | A1 | 10/2017 | Dobrinsky et al. |
| 2017/0333580 | A1 * | 11/2017 | Cahan ................... A61L 2/10 |
| 2017/0368215 | A1 | 12/2017 | Shatalov et al. |
| 2018/0028700 | A1 | 2/2018 | Dobrinsky et al. |
| 2018/0092308 | A1 | 4/2018 | Barber et al. |
| 2018/0104368 | A1 | 4/2018 | Dobrinsky et al. |
| 2018/0117194 | A1 | 5/2018 | Dobrinsky et al. |
| 2018/0185529 | A1 | 7/2018 | Shur et al. |
| 2018/0221521 | A1 | 8/2018 | Shur et al. |
| 2018/0243458 | A1 | 8/2018 | Shatalov et al. |

\* cited by examiner

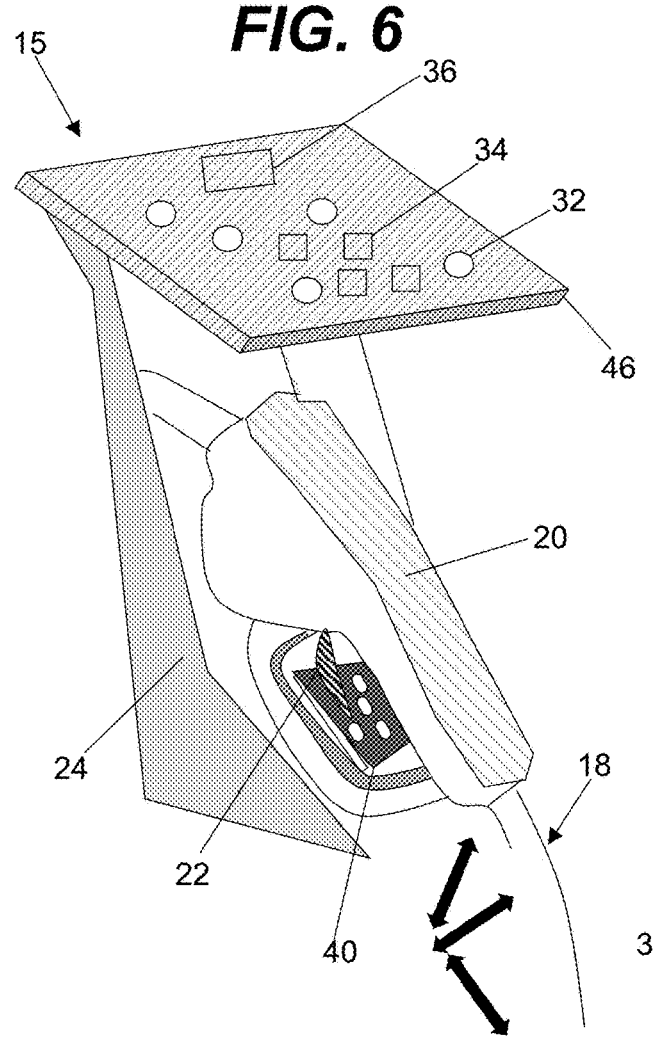
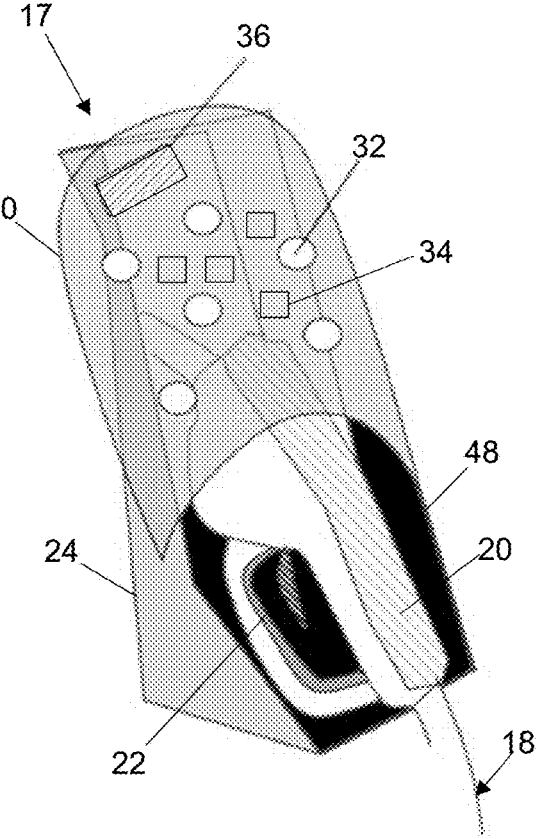

SURFACE TREATMENT WITH ULTRAVIOLET LIGHT

REFERENCE TO RELATED APPLICATIONS

The present patent application claims the benefit of U.S. Provisional Application No. 62/511,666, filed on 26 May 2017, which is hereby incorporated by reference.

TECHNICAL FIELD

The disclosure relates generally to cleaning surfaces in public places, and more specifically, to solutions for using ultraviolet radiation to treat (e.g., disinfect, sterilize, sanitize, and/or the like) a wide variety of surfaces in which people come into contact that are sources of microbes, bacteria, fungi, and the like, which can have harmful effects on one's health.

BACKGROUND ART

Gas pumps, automatic teller machines (ATMs), public bathrooms, door knobs and handles, vending machines, escalators, and kiosks with interactive screens and/or keypads are only a few examples of items in the general public with surfaces that are contacted by an inordinate amount of people that can harbor pathogens highly associated with illness and disease. *E-coli, salmonella* and *staphylococcus-aureus* are examples of types of bacteria that can be found on commonly-used surfaces that can be easily spread to those in the general public through contact with these surfaces. If untreated, these types of bacteria can have adverse effects on one's well-being such as serious illness and possibly death. Present approaches of treating commonly-used surfaces to prevent the spreading of microbial diseases typically include applying chemical disinfectants to the surfaces. While these chemical disinfectants can be effective at eradicating harmful bacteria, it is still difficult to effectively prevent the alarming rate in which the bacteria spreads within the general public. In addition, these chemical disinfectants can be harmful to the health of those that apply the chemicals to the commonly-used surfaces.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to solutions for using ultraviolet radiation to clean and treat (e.g., disinfect, sterilize, sanitize, and/or the like) a wide variety of surfaces in which people come into contact that are sources of microbes, bacteria, fungi, etc., which can have harmful effects on the well-being of those in the general public. Gas pumps, door knobs and handles, automatic teller machines (ATMs) and similarly related kiosks having interactive screens and/or keypads, and public rooms and spaces like bathrooms are a few examples of commonly-used items having surfaces that that can harbor pathogens that are highly associated with illness and disease. The various embodiments of the present invention provide effective solutions for cleaning and/or treating these surfaces to prevent the spreading of microbes, bacteria, fungi, and the like, that can have harmful effects on the well-being of those in the general public.

Each of the various embodiments described herein can utilize ultraviolet radiation as a primary modality to effectuate a surface treatment of commonly-used items. An ultraviolet light emitting diode (UV LED) based system is one type of system that can be used for the disinfection and the cleaning of commonly-used surfaces found in public. In particular, the UV LED based system can employ at least one UV LED source operating at a wavelength that ranges from about 200 nanometers (nm) to about 310 nm, with a range of 200 nm to 295 nm being most effective for sterilization and a range of 250 nm to 290 nm being optimal for ultraviolet germicidal action. Advantages of utilizing a UV LED based system include avoiding or reducing the use of chemical disinfectants which can have limited effectiveness in eradicating the spread of harmful bacterial and can be detrimental to the health of those that apply such chemicals.

In a gas station pump scenario in which a fuel nozzle having a handle and a trigger integrated with the handle are used to deliver fuel from a fuel dispenser, a solution provided by one embodiment of the present invention includes the use of at least one disinfection illuminator to irradiate operator or user contact surfaces on the fuel nozzle and the fuel dispenser with ultraviolet radiation. Each disinfection illuminator can include an open-ended enclosure that is attachably secured to the fuel dispenser. At least one ultraviolet radiation source can be integrated with the enclosure to emit ultraviolet radiation towards at least one of the user contact surfaces. In addition, the disinfection illuminator can include a control unit that determines whether any of the operator contact surfaces need a disinfection treatment.

In one embodiment, in this gas station pump scenario, a disinfection illuminator can be positioned about a mounting station in the fuel dispenser that stores the fuel nozzle while in a non-operational state. The open-ended enclosure of this disinfection illuminator forms a mounting station enclosure that is secured to the mounting station. In this manner, the at least one ultraviolet radiation source of the mounting station enclosure can irradiate the handle and the trigger of the fuel nozzle while resting in the mounting station during the non-operational state.

The mounting station enclosure can also include a trigger disinfection component coupled to the mounting station to irradiate the trigger and the underside of the handle. In one embodiment, the trigger disinfection component can be in a first location adjacent to the handle and the trigger while the fuel nozzle rests in the mounting station. The trigger disinfection component can be pivotably moveable from the first location to a second location underneath the handle and the trigger while the fuel nozzle rests in the mounting station. The second location enables the trigger disinfection component to provide wider irradiation coverage of the trigger and an underside of the handle during a treatment.

In one embodiment, in the gas station pump scenario, a disinfection illuminator can be positioned about an input/output console of the fuel dispenser that is used to facilitate a transaction for dispensing fuel. The open-ended enclosure of this disinfection illuminator forms an input/output console enclosure that is secured to the input/output console of the fuel dispenser. In this manner, the input/output console enclosure can irradiate input/output components that have user interaction during and after a fuel dispensing operation.

A variation of the above-noted disinfection illuminators can be used as a solution to treat door handles including door knobs and lever latch handles according to an embodiment of the present invention. For example, a disinfection illuminator with an open-ended enclosure can be attachably secured to a door about the door handle. At least one ultraviolet radiation source can be integrated with the enclosure to emit ultraviolet radiation towards the door handle. A control unit can determine whether the door handle needs a disinfection treatment and activate operation of the at least one ultraviolet source in response to determining that the door handle needs a disinfection treatment.

In an embodiment in which a door utilizes a door knob for opening and closing the door, the enclosure of the disinfection illuminator can include an open-ended cylindrical housing having a cavity formed therein that is configured to encircle the door knob. The cylindrical housing can include a plurality of ultraviolet radiation sources located over an entire surface area of the housing.

In an embodiment in which a door utilizes a lever latch handle for opening and closing door, the enclosure of the disinfection illuminator can include a bi-level enclosure having a first enclosure level located above the lever latch handle and a second enclosure level located underneath the lever latch handle. The first enclosure level and the second enclosure level can each include at least one ultraviolet radiation source to irradiate the lever latch handle. In one embodiment, the lever latch handle can be rotatable from a horizontal position that is used for opening and closing the door to a vertical position that is used for applying a disinfection treatment without having the capability to open and close the door. In one embodiment, the lever latch handle is outside an irradiation coverage range of the first enclosure and the second enclosure while in the horizontal position. Alternatively, the lever latch handle is inside the irradiation coverage range of the first enclosure and the second enclosure while in the vertical position.

In one embodiment, the lever latch handle can have a first set of handles and a second set of handles, wherein both the first and second set of handles includes a front handle located on a front side of the door and a back handle on the back side of the door. The first set of handles can be positioned in the horizontal position and the second set of handles can be positioned in the vertical position. Both the first and second set of handles can be rotatable between the horizontal position and the vertical position. To this extent, the door can include one of the first set of handles and the second set of handles in the horizontal position for opening and closing the door, while the other set of handles is in the vertical position ready for disinfection. The set of handles in the vertical position is configured for rotation to the horizontal position after disinfection for use in opening and closing the door. This permits the set of handles in the horizontal position to be moved to the vertical position for disinfection.

The disinfection illuminators used in the gas station pump and door handle scenarios can further include the use of at least one sensor to detect conditions (e.g., bacterial conditions) at the user contact surfaces and monitor the disinfection of the user contact surfaces. A variety of sensors are suitable for use with these embodiments. Possible sensors can include, but are not limited to, a visible sensor, an infrared sensor, a fluorescent sensor, chemical sensor, a radiation sensor, a pressure sensor, a temperature sensor, a humidity sensor, and a motion detector.

Another variation of the noted disinfection illuminators includes their use in solutions to treat user-interactive transaction devices such as automatic teller machines (ATMs) and similarly related kiosks having interactive screens and/ or keypads. For example, each of a plurality of disinfection illuminators can include a covering configured to irradiate a user interactive component that can have user contact to facilitate an aspect of a transaction. In one embodiment, each covering can be coupled to one of the user interactive components through a fastener mechanism. Each of the coverings can have at least one ultraviolet radiation source integrated with the enclosure that is configured to emit ultraviolet radiation towards a user contact surface associated with a corresponding user interactive component. In addition, each of the coverings can have at least one sensor configured to monitor conditions (e.g., bacterial conditions) at the user contact surfaces.

A control unit can be operatively coupled to the user interactive transaction device and the disinfection illuminators. The control unit can be configured to perform a multitude of operations. For example, the control unit can monitor conditions at the user contact surfaces of the various user interactive components through feedback provided by the sensors in each of the corresponding coverings. In this manner, the control unit can determine whether any of the user contact surfaces of the plurality of user interactive components require a treatment (e.g., disinfection) based on feedback of the conditions at the operator contact surfaces. To this extent, the control unit can activate operation of at least one ultraviolet source in any of the coverings associated with the user interactive components having user contact surfaces determined to be in need of a treatment.

In still another variation, the disinfection illuminators can be distributed throughout a public room such as a restroom and used to disinfect surfaces in the room. The disinfection illuminators can be distributed throughout the public room in locations having contact surfaces with higher incidences of human interaction. In one embodiment, each of the disinfection illuminators can be operatively coupled with each other based on human actions and/or inactions occurring in the locations within an operational range of the disinfection illuminators. For example, if a person failed to wash his or her hands after using a toilet in a restroom as noted by disinfection illuminators configured near the toilet and a sink, then an illuminator near the door to the restroom and an illuminator near a light switch can be activated to irradiate the surfaces of the door and the switch with ultraviolet radiation for disinfection purposes.

Each disinfection illuminator can include at least one ultraviolet radiation source configured to irradiate the contact surfaces within its operational range and at least one sensor configured to monitor conditions (e.g., bacterial conditions) at the contact surfaces within its operational range. A control unit can be operatively coupled to the disinfection illuminators in order to control the disinfection of the public room by the illuminators based on bacterial conditions in the public room and/or the actions or inactions taken by each person entering and leaving the room. The control unit can take the form of a centralized unit or configured as a distributed unit wherein operations of the control unit are distributed within each illuminator or groups of illuminators.

Operations performed by the control unit can include a variety of functions. For example, the operations can include, but are not limited to, monitoring bacterial conditions at the contact surfaces in the public room through feedback provided by the sensors from each of the disinfection illuminators, monitoring actions and/or inactions of each person entering and exiting the public room in vicinity of each of the disinfection illuminators, determining whether any of contact surfaces need a disinfection treatment based on feedback of the conditions at the contact surfaces, and/or the actions or inactions by each human entering and leaving the public room, activating operation of the ultraviolet radiation sources in any of the disinfection illuminators based on the occurrence of a predetermined amount of actions and/or inactions that are indicative of a possibility of proliferating bacterial contamination conditions, and facilitating a disinfection treatment of the contact surfaces that are in an irradiation range of coverage of each activated disinfection illuminator to remove the bacterial contamination conditions.

The operations performed by the control unit can be modified based on operator input. For example, the disinfection illuminators of the various embodiments can be configured with an input component that permits a user to adjust at least one of a variety of operating parameters used in the disinfection of the contact surfaces, and an output component that generates status information of the disinfection surface treatment for use by the user. The operating parameters that can be modified include, but are not limited to, a disinfection treatment time that the ultraviolet radiation sources emit ultraviolet radiation towards the contact surfaces, a dosage of ultraviolet radiation delivered by the sources, the power setting for operating the ultraviolet radiation sources, and a maximum operating temperature for the disinfection treatment. The status information that can be provided to the user via the output component can include, but is not limited to, the time remaining in a treatment operation, the effectiveness of the treatment, the date of the last treatment, special notifications pertaining to the quality of a prior or current disinfection treatment, etc.

The disinfection illuminators of the various embodiments described herein can be modified in a number of ways to improve the disinfection of the contact surfaces by the ultraviolet radiation sources. In particular, the internal surface of any of the enclosures having radiation sources used to irradiate a particular contact surface can include a coating or layer of material that promotes the recycling of the radiation back to the contact surfaces for further irradiation. For example, the internal surface of the enclosures can include a coating or layer of material that includes, but is not limited to, reflective material, ultraviolet reflective material, and diffusive reflective scattering material. In another embodiment, optical elements that can include, but are not limited to, lenses, mirrors, prisms and other reflective and light transmissive elements, and light guiding elements, can be configured with the enclosures to direct the ultraviolet radiation generated from the ultraviolet radiation sources to the user contact surfaces.

A first aspect of the invention provides a system for treating a fixture having at least one hand-operated device, comprising: a surface treatment unit configured to irradiate the at least one hand-operated device, the surface treatment unit including at least one disinfection illuminator having a covering coupled to the at least one hand-operated device, the covering including at least one ultraviolet radiation source that is configured to emit ultraviolet radiation towards user contact surfaces associated with the at least one hand-operated device, and at least one sensor configured to detect bacterial conditions at the user contact surfaces; and a control unit, operatively coupled to the surface treatment unit, that monitors bacterial conditions at the user contact surfaces of the at least one hand-operated device through feedback provided by the at least one sensor and determines whether any of the user contact surfaces of the at least one hand-operated device need a treatment based on at least one of: the feedback of the bacterial conditions at the user contact surfaces or an operational state of the at least one hand-operated device, the control unit activating operation of the at least one ultraviolet radiation source in response to determining that at least a portion of the user contact surfaces of the hand-operated device needs a treatment, wherein the activating includes specifying a plurality of operating parameters for the treatment, the plurality of operating parameters including a treatment time that the at least one ultraviolet radiation source emits the ultraviolet radiation towards the user contact surfaces, a dosage of ultraviolet radiation delivered by the at least one ultraviolet radiation source, a power setting for operating the at least one ultraviolet radiation source, and a maximum operating temperature for the treatment.

A second aspect of the invention provides a system, comprising: a user-interactive transaction device having a plurality of user interactive components each requiring user contact therewith to facilitate an aspect of a transaction, and a mounting station having a hand-operated device held therein at a predetermined position and orientation that is removable from the mounting station for performing a user-operated function relating to the transaction, the hand-operated device having a handle permitting a user to utilize the hand-operated device and an actuating mechanism that triggers operation of the hand-operated device; a surface treatment unit including a plurality of disinfection illuminators each having ultraviolet radiation sources configured to irradiate at least one of the plurality of user interactive components and the hand-operated device with ultraviolet radiation; and a control unit operatively coupled to the user interactive transaction device and the surface treatment unit, the control unit configured to control the ultraviolet irradiation of the plurality of user interactive components and the hand-operated device.

A third aspect of the invention provides a system, comprising: a door having a door handle on at least one side of the door for opening and closing the door; a disinfection illuminator configured to irradiate the door handle with ultraviolet radiation, the disinfection illuminator including an open-ended enclosure that is attachably secured to the door about the door handle; at least one ultraviolet radiation source integrated with the enclosure that is configured to emit ultraviolet radiation towards the door handle, and a control unit that determines whether the door handle needs a treatment, the control unit activating operation of the at least one ultraviolet source in response to determining that the door handle needs a treatment, wherein the activating includes specifying a plurality of operating parameters for the treatment, the plurality of operating parameters including a treatment time that the at least one ultraviolet radiation source emits the ultraviolet radiation towards the door handle, a dosage of ultraviolet radiation delivered by the at least one ultraviolet radiation source, a power setting for operating the at least one ultraviolet radiation source, and a maximum operating temperature for the treatment.

A fourth aspect of the invention provides a system, comprising: a fuel nozzle to deliver fuel, the fuel nozzle having a handle to grip the fuel nozzle and a trigger integrated with the handle that releases the fuel through the fuel nozzle in response to actuation of the trigger; a fuel dispenser configured to dispense fuel through the fuel nozzle, the fuel dispenser having a mounting station to store the fuel nozzle in a non-operational state and an input/output console that facilitates dispensing of the fuel; at least one disinfection illuminator configured to irradiate user contact surfaces on the fuel nozzle and the fuel dispenser with ultraviolet radiation, the at least one disinfection illuminator including an open-ended enclosure that is attachably secured to the fuel dispenser, at least one ultraviolet radiation source integrated with the enclosure that is configured to emit ultraviolet radiation towards at least one of the user contact surfaces, and a control unit that determines whether any of the user contact surfaces needs a treatment, the control unit activating operation of the at least one ultraviolet radiation source in response to determining that at least one of the user contact surfaces needs a treatment, wherein the activating includes specifying a plurality of operating parameters for the treatment, the plurality of operating parameters including: a treatment time that the at least one ultraviolet radiation source emits the ultraviolet radiation towards the user contact surfaces, a dosage of ultraviolet radiation delivered by the at least one ultraviolet radiation source, a power setting for operating the at least one ultraviolet radiation source, and a maximum operating temperature.

A fifth aspect of the invention provides a system, comprising: a user-interactive transaction device having a plurality of user interactive components each requiring user contact therewith to facilitate an aspect of a transaction; a surface treatment unit configured to irradiate each of the plurality of user interactive components with ultraviolet radiation, the surface treatment unit including a plurality of disinfection illuminators, each disinfection illuminator having a covering coupled to one of the plurality of user interactive components, each covering including at least one ultraviolet radiation source that is configured to emit ultraviolet radiation towards user contact surfaces associated with a corresponding user interactive component and at least one sensor configured to monitor conditions at the user contact surfaces; and a control unit operatively coupled to the user interactive transaction device and the surface treatment unit, the control unit configured to perform operations that include: monitoring conditions at the user contact surfaces of the plurality of user interactive components through feedback provided by the at least one sensor of each of the corresponding coverings; determining whether any of the user contact surfaces of the plurality of user interactive components need a treatment based on feedback of the conditions at the user contact surfaces; and activating operation of the at least one ultraviolet source in any of the coverings associated with the plurality of user interactive components having user contact surfaces in need of a treatment, wherein the activating includes specifying a plurality of operating parameters for the treatment, the plurality of operating parameters including a cleaning treatment time that the at least one ultraviolet radiation source emits the ultraviolet radiation towards the user contact surfaces, a dosage of ultraviolet radiation delivered by the at least one ultraviolet radiation source, a power setting for operating the at least one ultraviolet radiation source, and a maximum operating temperature.

A sixth aspect of the invention provides a system for treating a public room having a plurality of contact surfaces subject to proliferation of bacterial contamination through human interaction with the public room, the system comprising: a plurality of disinfection illuminators distributed throughout the public room in locations having contact surfaces with higher incidences of human interaction, each of the plurality of disinfection illuminators operatively coupled with each other based on human actions and/or inactions occurring in the locations that are within an operational range of each of the disinfection illuminators, each disinfection illuminator including: at least one ultraviolet radiation source configured to irradiate the contact surfaces within the operational range; and at least one sensor configured to monitor bacterial conditions at the contact surfaces within the operational range; and a control unit, operatively coupled to the plurality of disinfection illuminators, that controls the treatment of the public room by the plurality of disinfection illuminators based on bacterial conditions in the public room and the actions and/or inactions taken by each human entering and leaving the room.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 6 shows a schematic view of a disinfection illuminator configured to disinfect the top side of the handle of a fuel nozzle and an underside of the nozzle including the trigger while in the mounting station during a non-operational state according to an embodiment.

FIG. 7 shows a schematic view of a disinfection illuminator depicted in FIG. 2 having a coating of material on the internal surface to promote recycling of the ultraviolet radiation for further disinfection of the fuel nozzle according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1A:
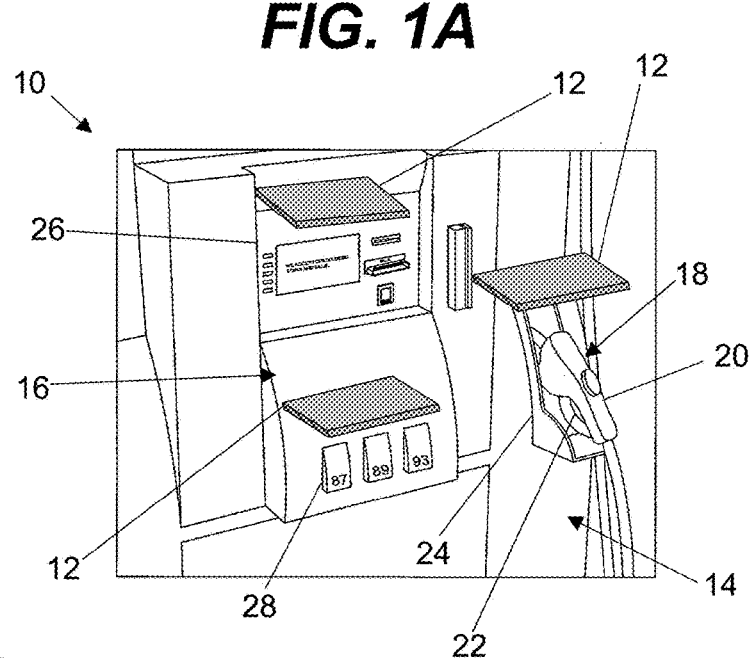
FIGS. 1A-1C show a schematic of a system having disinfection illuminators for treating a gas station pump including a fuel dispenser and a fuel nozzle having a handle and a trigger according to an embodiment.

As indicated above, aspects of the invention are directed to using ultraviolet radiation to treat (e.g., disinfect, sterilize, sanitize, and/or the like) a wide variety of surfaces in which people come into contact that are sources of microbes, bacteria, fungi, and the like, and that can have harmful effects on the well-being of those in the general public. Gas station pumps, door knobs and handles, automatic teller machines (ATMs) and similarly related kiosks having interactive screens and/or keypads, and public bathrooms are a few examples of commonly-used items or fixtures having surfaces that can harbor pathogens that are highly associated with illness and disease in which embodiments of the present invention use disinfection illuminators or surface treatment units formed from these illuminators to provide effective solutions for cleaning and treating these surfaces to prevent the spreading of microbes, bacteria, fungi, and the like. Although the description that follows is directed to using these disinfection illuminators to treat gas station pumps, door knobs and handles, ATMs and similarly related kiosks having interactive screens and/or keypads, and public bathrooms, it is understood that these components can be configured for use with a multitude of devices or fixtures, and locations having contact surfaces that are commonly used by those in the general public that have a need for a treatment due to the build-up of harmful pathogens that can have deleterious effects on the well-being of those that come in contact with these surfaces such as, for example, buttons used in elevators, and street crossing buttons. The modalities used with the disinfection illuminators for any of the systems described herein can include any now known or later developed approaches that incorporate the concepts of these embodiments.

As used herein, a treatment of commonly-used contact surfaces in the general public can entail sanitizing, disinfecting, and/or sterilizing these surfaces. Sanitizing generally means reducing the number of bacterial contaminants to a predetermined safe level. Disinfecting generally means destroying pathogenic and other types of microorganisms, while sterilizing can be more extensive in that it kills all microbial forms and/or include destroying the ability of the microbial forms to reproduce. In the description that follows with regard to the various embodiments, disinfecting, a disinfection or a disinfection treatment of a surface performed by any of the disinfection illuminators or disinfection treatment units described herein means a cleaning treatment of that surface that includes sanitizing, disinfecting, and/or sterilizing the surface.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, ultraviolet-C (UV-C) electromagnetic radiation having a wavelength ranging from approximately 200 nm to approximately 280 nm, and vacuum ultraviolet (vacuum UV) electromagnetic radiation having a wavelength ranging from approximately 10 nm to approximately 200 nm.

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 290 nm provides the highest germicidal effectiveness, while an ultraviolet radiation between about 200 nm to about 310 nm is sufficient for providing overall germicidal effectiveness of commonly-used surfaces found in the general public. While susceptibility to ultraviolet radiation varies, exposure to ultraviolet energy in the above range of about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through. Also, unless otherwise noted, the term "set" means one or more (i.e., at least one) and the phrase "any solution" means any now known or later developed solution.

Figure 1B:
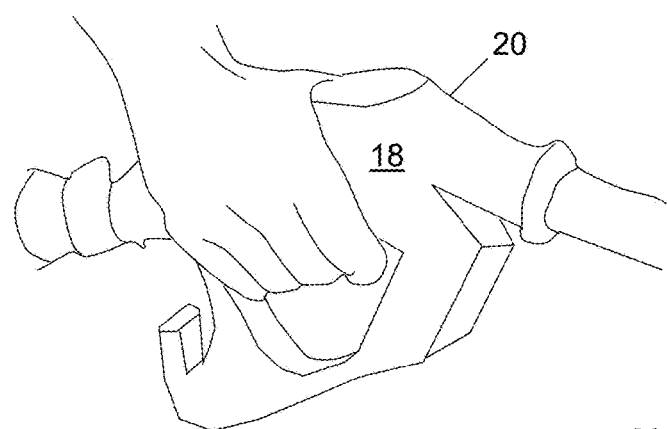
Figure 1C:
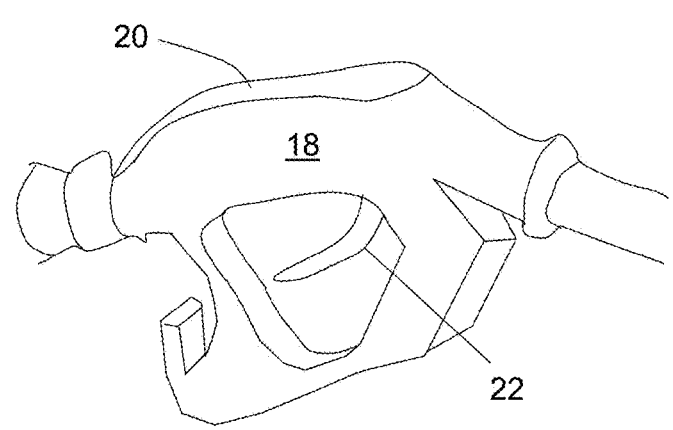

Turning to the drawings, FIGS. 1A-1C show a schematic of a system 10 having disinfection illuminators 12 for disinfecting a gas station pump assembly 14 including a fuel dispenser 16 that dispenses fuel from underground tanks (not shown) through a fuel nozzle 18 having a handle 20 and a trigger 22 according to an embodiment. FIG. 1A shows that the fuel dispenser 16 includes a mounting station 24 that is configured to store the fuel nozzle 18 in a non-operational state, while FIGS. 1B-1C show the fuel nozzle 18 removed from the mounting station 24 ready for a fuel dispensing or releasing operation once the trigger 22 has been actuated (e.g. depressed) as shown in FIG. 1B. The fuel dispenser 16 also includes an input/output console 26 and fuel grade (e.g., 87 octane fuel, 89 octane fuel and 93 octane fuel) selector 28 that facilitate the dispensing of the fuel. For example, the input/output console 26 can include user interactive components such as selection buttons for facilitating payment of the fuel dispensing transaction, a display that can provide information regarding the payment, payment card slots for entering credit/debit cards, and a printer for printing receipts. Similarly, the fuel grade selector 28 can include user interactive components such as selection buttons that enable a customer to select a particular fuel grade to be dispensed from the fuel dispenser 16 and fuel nozzle 18. It is understood that the gas station pump assembly 14 including the fuel dispenser 16 and the fuel nozzle 18 can include additional components (e.g., ethanol fuel selection, promotional displays), and those skilled in the art will appreciate that the disinfection illuminators 12 are applicable to gas station pump assemblies that differ from the one depicted in FIG. 1A.

Further, the various buttons, selectors, displays, card slots, and printers located about the fuel dispenser 16 and the fuel nozzle 18 with handle 20 and trigger 22 are considered to be hand-operated devices because a hand of a user or parts of the hand such as fingers are generally necessary to engage their use. It is understood that these examples of hand-operated devices are not meant to limit this embodiment and others described herein that use other types of hand-operated devices. For instance, door knobs and door latches are examples of hand-operated devices associated with a door, like card slots, keypads, input screens, and printers are hand-operated devices with an ATM or similar kiosk device configuration, as bathroom lights, sinks, hand dryers, toilet flush handles, paper towel dispensers, etc., are hand-operated devices in a public bathroom scenario.

Referring back to FIG. 1A, the disinfection illuminators 12 are positioned at locations about the gas station pump assembly 14 where there are a high incidence of user or customer contact with the assembly. For example, the disinfection illuminators 12 are located about the typical surfaces that a customer will contact while using the gas station pump assembly 14 during a fill-up operation. In one embodiment, a disinfection illuminator 12 can be positioned about the mounting station 24 in order to disinfect the gripping portion of the handle 20 that a user will typically grasp to pull the fuel nozzle 18 from the station, and to hold onto while depressing the trigger 22 during a fuel dispensing operation. The disinfection illuminator 12 about the mounting station 24 can also disinfect the surface of the trigger 22 that is contacted by each user that uses the gas station pump assembly 14 to dispense fuel from the fuel dispenser 16. FIG. 1A also shows a disinfection illuminator 12 located about the input/output console 26 and another illuminator located about the fuel grade selector 28 to disinfect each of their user interactive components (e.g., buttons, slots, displays, printers) that a user may have contact with in a typical fill-up operation.

The disinfection illuminators 12 can take the form of open-ended enclosures that overhang the mounting station 24, the input/output console 26 and the fuel grade selector 28 in an attachably secure manner. For example, the disinfection illuminators 12 can be secured to the mounting station 24, the input/output console 26 and the fuel grade selector 28 by a fastener mechanism that can include, but is not limited to, a magnetic coupler, clips, tabs, hook and loop fasteners, mechanical fasteners (e.g., threaded connections), friction type fastening devices, etc.

It is understood that the disinfection illuminators 12 are not meant to be limited to an overhang configuration. These disinfection illuminators 12 can be positioned to the bottom and the sides of the mounting station 24, the input/output console 26 and the fuel grade selector 28, and in some embodiments, the illuminators can substantially enclose the top, the sides and bottom portions of these components of the gas station pump assembly 14 while having an open region that enables sufficient user contact with these components to operate in their intended manner. Furthermore, it is understood that the locations of the disinfection illuminators 12 as depicted in FIG. 1A are for illustrative purposes and not meant to be limiting, as these illuminators can be positioned about other locations of the gas station pump assembly 14 that have user contact and that can be regions that are subject to contaminant build-up.

Although not shown in FIG. 1A for purposes of clarity, but shown in figures of other embodiments described herein, the disinfection illuminators 12 can have at least one ultraviolet radiation source integrated with the enclosure of the illuminators that is configured to emit ultraviolet radiation towards the user contact surfaces associated with the fuel nozzle 18 including the handle 20 and the trigger 22, the input/output console 26 and the fuel grade selector 28. In addition, the disinfection illuminators 12 can include at least one sensor to monitor the conditions of the user contact surfaces associated with the corresponding component of the gas station pump assembly 14 with which each illuminator is designated to operate. The at least one sensor can include, but is not limited to, a visible sensor, an infrared sensor, a bacterial fluorescent sensor, a temperature sensor, a pressure sensor, a chemical sensor, a radiation sensor (e.g., an ultraviolet dose counter or meter), a humidity sensor, and/or combinations thereof. Also, each of the disinfection illuminators 12 can include a control unit that manages the irradiation of the contact surfaces by the ultraviolet radiation sources. This can include, but is not limited to operations such as determining whether any of the operator contact surfaces need a treatment, activating operation of ultraviolet radiation sources responsible for irradiating surfaces deemed to need a treatment, and monitoring the conditions (e.g., bacterial conditions) at the various contact surfaces during and after the treatment.

Each ultraviolet radiation source that is used with a disinfection illuminator 12 can adhere to an inner surface of the illuminator's enclosure. In this manner, each ultraviolet radiation source can be configured to emit ultraviolet radiation towards a specific contact surface associated with the gas station pump assembly to effectuate a disinfection treatment. In one embodiment, each disinfection illuminator 12 associated with the mounting station 24, the input/output console 26 and the fuel grade selector 28 can have a set of ultraviolet radiation sources configured to emit ultraviolet radiation towards the user contact surfaces associated with the fuel nozzle 18 including the handle 20 and the trigger 22, and the various user interactive components of the input/output console 26 and the fuel grade selector 28, respectively.

The set of ultraviolet radiation sources can comprise any combination of one or more ultraviolet radiation emitters. Examples of ultraviolet radiation emitters can include, but are not limited to, high intensity ultraviolet lamps (e.g., high intensity mercury lamps), discharge lamps, UV LEDs, super luminescent LEDs, laser diodes, and/or the like. In one embodiment, the set of ultraviolet radiation sources can include a set of LEDs manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). These group-III nitride semiconductors can be designed to emit a wavelength at a specific peak wavelength with a narrow bandwidth such as a few tens of nanometers (e.g., approximately 40 nanometers or less). Additionally, the set of ultraviolet radiation sources can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a waveguide, a plurality of ultraviolet fibers, each of which terminates at an opening, a diffuser, and/or the like.

Figure 2:
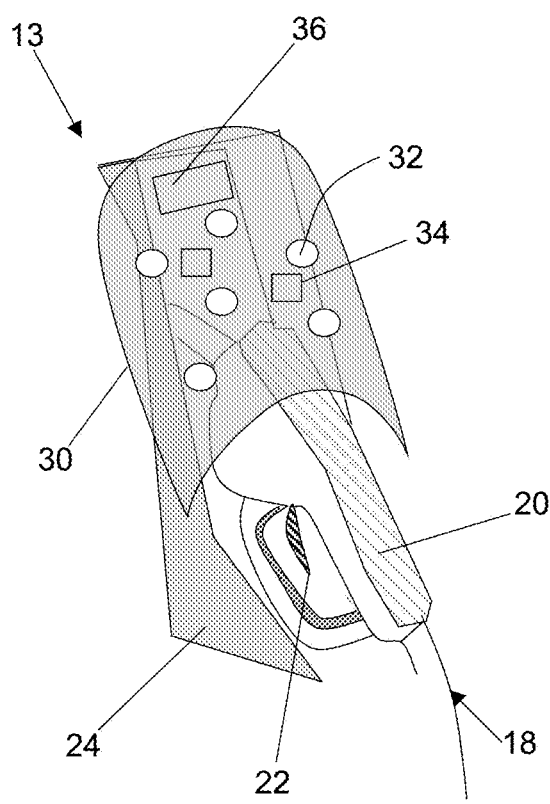
FIG. 2 shows a more detailed view of a disinfection illuminator located about a fuel nozzle while resting in a non-operational state according to an embodiment.

FIG. 2 shows a more detailed view of a disinfection illuminator 13 located about a mounting station 24 for disinfecting a fuel nozzle 18 while resting in a non-operational state in the station according to an embodiment. In this embodiment, the enclosure of the disinfection illuminator 13 can take the form of a mounting station enclosure 30 that is secured to the mounting station 24 of the fuel dispenser (not shown in FIG. 2) and configured to irradiate the handle 20 and the trigger 22 of the fuel nozzle 18 while resting in the mounting station during the non-operational state.

The mounting station enclosure 30 can be attachably secured to the mounting station by any one of the aforementioned fastener mechanisms. For example, in one embodiment, the mounting station enclosure 30 can be secured to the mounting station 24 by screws, clips, hook and loop fasteners, adhesive, and/or the like. As shown in FIG. 2, the mounting station enclosure 30 can enclose a top portion and side portions of the mounting station 24 leaving the bottom portion open so that the fuel nozzle 18 can be easily removed from and inserted into the station without being obstructed by the enclosure. With the open-ended mounting station enclosure 30, the disinfection illuminator 13 can be used to irradiate the handle 20 and the trigger 22 of the fuel nozzle 18 with ultraviolet radiation to facilitate a disinfection treatment after a user has used the nozzle to dispense fuel, or after it has been determined that the handle and trigger have bacterial conditions that warrant a treatment. The disinfection illuminator 13 is configured to perform a disinfection treatment of the handle 20 and the trigger 22 once the fuel nozzle 18 is docked in the mounting station 24.

It is understood that the mounting station enclosure 30 is not meant to be limited to any one particular configuration. Those skilled in the art will appreciate that the enclosure can actually enclose the handle 20 and the trigger 22 of the fuel nozzle while resting in the mounting station 24. For example, in one embodiment, the enclosure 30 can include a set of movable shutters that surround the handle and trigger while the fuel nozzle is in the mounting station. The shutters can be automatically or manually opened to provide access to the fuel nozzle and shut upon insertion in the mounting station 24 for applying a disinfection treatment.

FIG. 2 shows that the mounting station enclosure 30 of the disinfection illuminator 13 can include a set of ultraviolet radiation sources 32 to irradiate the contact surfaces of the handle 20 and the trigger 22, a set of sensors 34 to monitor the conditions of the operator contact surfaces associated with the handle and the trigger including bacterial conditions, and a control unit 36 that manages the irradiation of the contact surfaces by the ultraviolet radiation sources. In one embodiment, the set of ultraviolet radiation sources 32 and the set of sensors 34 can be located on the internal surface of the mounting station enclosure 30, while the control unit 36 can be located on the external surface of the enclosure and be operatively in communication with the sources and the sensors. It is understood that the set of ultraviolet radiation sources 32, the set of sensors 34 and the control unit 36 can be located on other portions of the mounting station enclosure 30. For example, the set of ultraviolet radiation sources 32 can be attached to the external surface of the mounting station enclosure 30. In this manner, each ultraviolet radiation source can direct ultraviolet radiation through a corresponding ultraviolet transparent window formed in the enclosure and onto a designated surface contact area of the handle 20 and/or the trigger 22.

It is understood that the number of ultraviolet radiation sources 32 and sensors 34 illustrated in FIG. 2 is representative of only one possible configuration. Those skilled in the art will appreciate that any number of ultraviolet radiation sources 32 and sensors 34 may be located about either the internal or external surface of the mounting station enclosure 30. For example, the mounting station enclosure 30 can have only one ultraviolet radiation source 32 and sensor 34 positioned along the inner surface (e.g. at a central portion) of the mounting station enclosure 30, or there can be multiple ultraviolet radiation sources 32 and sensors 34 located at the same position along the inner surface or at varying locations. For example, multiple ultraviolet radiation sources 32 positioned at varying locations can be used to irradiate the same surface or overlapping subset of surfaces (e.g., multiple user contact surfaces of a pump handle).

In order to effectuate a disinfection treatment of a contact surface of the handle 20 and the trigger 22, the ultraviolet radiation sources 32 can be configured to be operated at a number of wavelengths. For example, in one embodiment, the ultraviolet radiation sources 32 can be configured to operate at a wavelength that ranges from about 200 nm to about 310 nm, with a wavelength that ranges from about 250 nm to about 290 nm providing the highest germicidal effectiveness. Emission of ultraviolet light within these ranges for a predetermined time period (e.g., 10 minutes) is typically sufficient to provide an ultraviolet dose that effectively cleans the handle 20 and the trigger 22 from a germicidal effectiveness point of view.

In one embodiment, the ultraviolet radiation sources 32 can be configured to function in a coordinated manner. For example, the ultraviolet radiation sources 32 can operate at the same wavelengths and intensities for the same duration, or the sources can operate at different wavelengths and intensity for varying durations. In one embodiment, a first set of ultraviolet radiation sources 32 can operate at a target wavelength and intensity that is designed for the disinfection of one type of bacteria and/or viruses, while a second set of ultraviolet radiation sources 32 can operate at a different target wavelength and intensity that is designed for disinfection of a different type of bacteria and/or viruses.

Although not shown in FIG. 2, the mounting station enclosure 30 can include a sensor or the like that determines when the fuel nozzle 18 is inserted into and removed from the station. In this manner, the control unit 36 can manage the set of ultraviolet radiation sources 32 and sensors 34 to perform a disinfection treatment only when the sensor integrated in the mounting station 24 detects when the fuel dispensing portion of the fuel nozzle 18 is positioned in the mounting station 24 in a non-operational state. Examples of this sensor in the mounting station 24 can include, but is not limited to, a pressure sensor, a proximity sensor (e.g., a capacitance, optical, magnet proximity sensor), a motion detection sensor (e.g., laser/photodiode couple, pressure sensor, and/or the like) to determine whether or not the fuel nozzle 18 has been removed from or inserted into the mounting station 24, or combinations thereof. In one embodiment, a pressure sensor can measure the pressure experienced by the mounting station 24, while a proximity sensor can determine the proximity of the fuel dispensing portion of the fuel nozzle 18 to its resting position in the station. In either case, these sensors can generate signals representative of the conditions that each are configured to detect and send those signals to the control unit 36 which determines when the fuel dispensing portion of the fuel nozzle 18 and the handle 20 are secure within the mounting station 24.

Once it is determined that the fuel nozzle 18 is in the mounting station 24 in a non-operational state, the control unit 36 can use the set of sensors 34 to determine whether any of the contact surfaces of the handle 20 including the trigger 22 are in need of a disinfection treatment. In one embodiment, at least one of the sensors 34 in the mounting station can include a bacterial fluorescence sensor that can detect the amount or presence of bacteria, germs, viruses, and/or the like, which is present on any of the user contact surfaces of the handle 20 and the trigger 22. To this extent, the bacterial fluorescence sensor can generate signals representative of the bacterial conditions of the user contact surfaces of the handle 20 and the trigger 22 with respect to the amount of bacteria, germs, viruses, pathogens, and the like, and send those signals to the control unit 36. The control unit 36 can determine whether a disinfection treatment is necessary as a function of the signals provided by the bacterial fluorescence sensor using any solution.

In one embodiment, the control unit 36 can activate the operation of the ultraviolet radiation sources 32 in response to determining that any of the user contact surfaces of the handle 20 and the trigger 22 have an amount of bacteria, germs, viruses, and/or the like, which exceeds a predetermined threshold, and thus, requiring a disinfection treatment. Activating the operation of the ultraviolet radiation sources 32 by the control unit 36 can include specifying a plurality of operating parameters for the disinfection treatment of any of the user contact surfaces of the handle 20 and the trigger 22 deemed to have conditions warranting the treatment. In one embodiment, the plurality of operating parameters can include, but are not limited to, a disinfection cleaning treatment time that the ultraviolet radiation sources 32 emit the ultraviolet radiation towards the user contact surfaces, a dosage of ultraviolet radiation delivered by the ultraviolet radiation sources 32, a power setting for operating the ultraviolet radiation sources 32, and a maximum operating temperature for the disinfection treatment. It is understood that these operating parameters are illustrative of some of the parameters that can be set by the control unit 36 and are not meant to be limiting as other parameters exist which may be specified such as for example, a wavelength of the ultraviolet light used for the disinfection.

Furthermore, it is understood that the sensors 34 can include a multitude of other different types of sensors and that this embodiment as well as the other embodiments of the present invention are not meant to be limited to the aforementioned bacterial fluorescence sensor, pressure sensor, humidity sensor and proximity sensor. Other sensors that are suitable for use with the set of sensors 34 in the mounting station enclosure 30 can include, but are not limited to, an infrared sensor, a temperature sensor, a chemical sensor, and a radiation sensor (e.g., an ultraviolet dose counter or meter), etc. Each of these sensors can detect the level or amount of a particular parameter that each is intended to measure and send signals thereof to the control unit 36. For example, a temperature sensor can detect the temperature about the mounting station 24 underneath the enclosure 30 and/or the temperature of the user contact surfaces of the handle 20 and the trigger 22, an infrared sensor can detect the amount of heat on the handle from the heat transferred from a person using the fuel nozzle, a chemical sensor can detect a level of a particular chemical that resides on any of the surfaces that are to be irradiated with the ultraviolet radiation, and a radiation sensor can detect a level of radiation that is present about the mounting station 24 underneath the enclosure 30.

These sensors along with any of the aforementioned fluorescence, pressure, and proximity sensors can be deployed along with the ultraviolet radiation sources 32 in any desired configuration. For example, the sensors 34 can be interspersed with the ultraviolet radiation sources 32 or separated from each other. In addition to the aforementioned sensors, the enclosure can be configured with a visible camera configured to detect the presence of contamination on the handle 20. In addition, the camera can be used to detect the presence of a person in proximity of the handle 20; which can be used to alter timing and/or duration of the ultraviolet irradiation.

The control unit 36 can include a timer with switches and/or the like, to manage the duration that the ultraviolet radiation sources 32 are on for a particular disinfection treatment, and ensure that radiation is applied to a particular user contact surface of the fuel nozzle 18 for that duration. In one embodiment, the control unit 36 operating in conjunction with the timer can manage the amount of time that the ultraviolet radiation sources 32 radiate in the UV-C range versus the UV-B range. The duration and frequency treatment that the ultraviolet radiation sources 32 are utilized can depend on detected condition signals provided to the control unit 36 by any of the sensors 34, as well as any other predetermined treatment factors such as the length of time that has passed since the fuel nozzle 18 has been used, areas of the nozzle that have had user contact when in use, and whether a set predefined treatment schedule is being followed. Generally, an effective disinfection treatment time can range from a fraction of a minute to about ten or even twenty minutes. The intensity and duration of treatment can be calibrated depending on a frequency of use of the fuel nozzle 18.

During operation of a disinfection treatment, the control unit 36 can be used to control at least one of a plurality of predetermined ultraviolet radiation characteristics associated with the ultraviolet radiation emitted from the ultraviolet radiation sources 32. The predetermined ultraviolet radiation characteristics that can be controlled by the control unit 36 can include wavelengths, intensities, and durations and/or the like. In one embodiment, the control unit 36 can control the wavelength of ultraviolet radiation and intensity spatially over any of the user contact surfaces of the fuel nozzle 18. As an example, the control unit 36 can control the ultraviolet radiation sources 32 to operate at a target wavelength and intensity for a duration that is designed for the disinfection of bacteria and/or viruses on the surfaces of the handle 20 and the trigger 22. In one embodiment, the control unit can calculate an amount of radiation that is designed to deliver a necessary dose to the surfaces of the handle 20 and the trigger 22 for a duration of a time that is sufficient for disinfection of the surfaces, and thus be completely treated before the next use of the nozzle.

In an embodiment, the control unit 36 can determine the target intensity of the radiation based on an amount of time since a previous disinfecting treatment has been performed. In an embodiment, the treatment can be administered either directly after the use of the handle 20, or after a set period of time. The set period of time can be selected based on the environmental conditions around the pump handle. In an embodiment the set period of time can be in a range between twenty to thirty minutes. In an alternative embodiment, a set of UV-A radiation sources can be employed between the disinfection periods, in order to prevent microbial growth between disinfection periods. In an embodiment, the UV-A sources can comprise ultraviolet light emitting diodes radiating in the wavelength of 380-460 nm. In another embodiment, the photo-catalyst can be present within the proximity of handle 20 in order to generate hydroxyl group elements capable of enhancing disinfection of the handle 20.

The intensity range can be determined based on attributes of the ultraviolet radiation sources 32. The target intensity can be incremented in steps or continuously over the range of times corresponding to the varying intensities. The range of times can be determined based on, for example, feedback data acquired regarding a severity of contamination typical for a period of time. In an embodiment, the control unit 36 can generate a warning signal for presentation to a user when the time period since a previous disinfection has exceeded a maximum recommended time (e.g., time period corresponding to the maximum ultraviolet radiation). The warning signal can be generated using any type of output device including, for example, a vibration device, a visible light (e.g., flashing), an auditory signal generated by a speaker, and/or the like.

In addition, during the operation of the disinfection treatment, the control unit 36 can be used to turn on or off the ultraviolet radiation sources 32 dependent upon the detected conditions provided by the sensors 34. In one embodiment, the control unit 36 can turn on or off each of the ultraviolet radiation sources 32 via an actuator. Also, the control unit 36 can be used to adjust one or more of the ultraviolet radiation characteristics based on the conditions detected by the sensors 34. For example, the control unit 36 can use the signals from a bacterial fluorescence sensor that are representative of the amount of bacteria, germs, viruses, and/or the like, present on any of the user contact surfaces to adjust the intensity, the wavelength, the duration and or the pattern of the ultraviolet radiation emitted from any of the ultraviolet radiation sources 32. In another embodiment, the control unit 36 can be configured to interrupt the operation of the ultraviolet radiation sources 32 in response to receiving temperature signals from a temperature sensor and determining that the temperature of the disinfection treatment has exceeded the maximum temperature. The control unit 36 can resume the disinfection treatment after a predetermined cooling time has elapsed.

The control unit 36 can also include a wireless transmitter and receiver that is configured to communicate with a remote location via Wi-Fi, BLUETOOTH, and/or the like. As used herein, a remote location is a location that is apart from the mounting station 24 (e.g., in the gas station store that accompanies the fuel pump assembly). For example, a remote computer can be used to transmit operational instructions to the wireless transmitter and receiver. The operational instructions can be used to program functions performed and managed by the control unit 36. In another embodiment, the wireless transmitter and receiver can transmit cleaning treatment results, data from the sensors 34 to the remote computer, to facilitate maintenance and diagnostic operations on the mounting station enclosure 30.

The control unit 36 can include an input component and an output component to allow a user to interact with the mounting station enclosure 30 and the control unit itself, and to receive information from the enclosure during the disinfection treatment. In one embodiment, the input component can permit a user to adjust at least one of the aforementioned plurality of operating parameters. This can include making adjustments during the disinfection treatment operation and/or prior to initiating a treatment. In one embodiment, the input component can include a set of buttons and/or a touch screen to enable a user to specify various input selections regarding the operating parameters as well as the disinfection treatment. In one embodiment, the output component can include a visual display for providing status information on the disinfection treatment (e.g., time remaining, the presence of bacteria, viruses, germs or the like), an indication that a disinfection treatment is recommended, an indication that the user contact surfaces of the fuel nozzle 18 has been sterilized, disinfected, or sanitized, an indication that the nozzle has been disinfected or sanitized, an indication after its last use, a simple visual indicator that displays whether a disinfection treatment is underway (e.g., an illuminated light) or if the treatment is over (e.g., absence of an illuminated light).

The mounting station enclosure 30 can further include a power source that is configured to power each of the ultraviolet radiation sources 32, the sensors 34, and the control unit 36. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source for the mounting station enclosure 30 can include a mechanical energy to electrical energy converter such as a piezoelectric crystal, and a rechargeable device.

Figure 14:
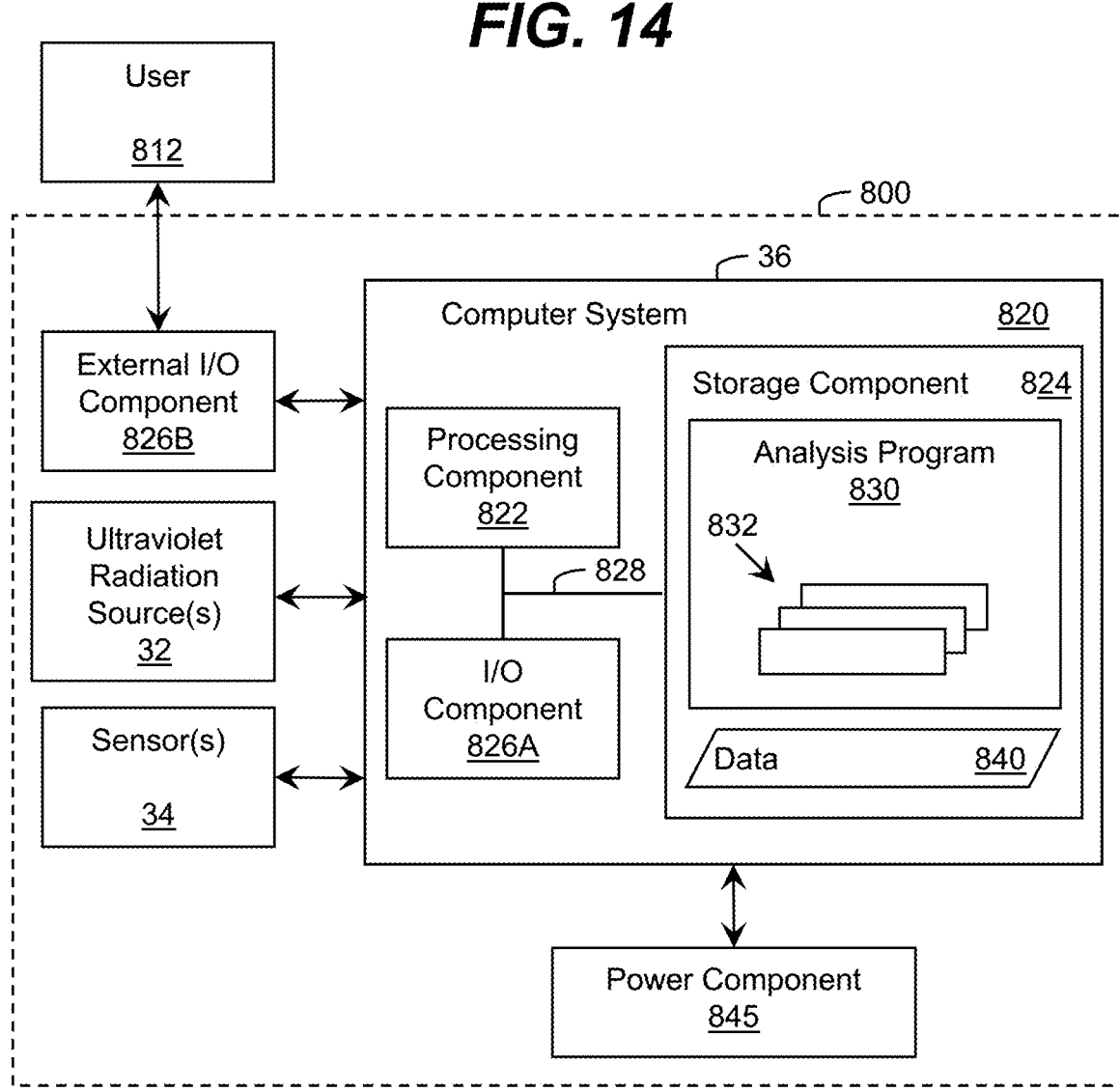
FIG. 14 shows a schematic block diagram representative of an overall processing architecture according to an embodiment that is applicable to any of the systems described herein that include any of the disinfection illuminators.

The aforementioned components of the mounting station enclosure 30 are illustrated in FIG. 14 and discussed further with regard to this figure. These components of the mounting station enclosure 30 are also suitable for use with any of the enclosures associated with the disinfection illuminators 12 depicted in FIG. 1A. For example, these components can be configured with the disinfection illuminator 12 located about the input/output console 26 in FIG. 1A, as well as the disinfection illuminator 12 located about the fuel grade selector 28. In this manner, the disinfection illuminator 12 located about the input/output console 26 can include an input/output console enclosure that is secured to the input/output console that is configured to irradiate input/output components, while the disinfection illuminator 12 located about the fuel grade selector 28 can include a fuel grade selector enclosure that is secured adjacent the fuel grade selector that is configured to irradiate the fuel grade selector buttons. These enclosures can include the same components as those described above with respect to the mounting station enclosure 30 and operate in a similar manner. However, it is understood that the components of the enclosures corresponding to the input/output console 26 and the fuel grade selector 28 can be configured specifically to operate in consideration of the actions performed by these parts of the gas station pump assembly as well as the user contact that generally occurs at a typical fuel transaction.

Also, it is understood that the functions of these components (i.e., the ultraviolet radiation sources 32, the sensors 34 and the control unit 36) are also applicable and suitable for use with any of the other disinfection illuminators described with regard to the various embodiments of the present invention described herein such as those illustrated in the other figures. For clarity, a full description of the ultraviolet radiation sources 32, the sensors 34 and the control unit 36 for the disinfection illuminators of these other embodiments is not repeated.

It is understood that the functions of these components in the various disinfection illuminators can vary and will depend on the particular application and environment that each illuminator is used. Thus, the above functions described with respect to FIG. 2 are only illustrative of examples of particular functions and operations to be performed and are not meant to be limiting to the embodiment of FIG. 2 as well as to any of other embodiments described herein that utilize disinfection illuminators.

Figure 3:
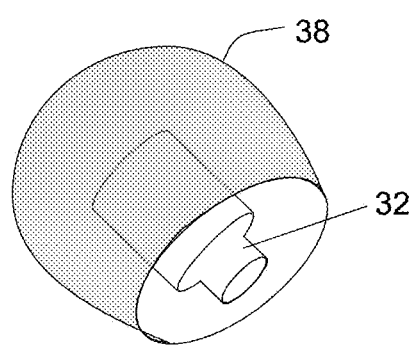
FIG. 3 shows a more detailed view of an ultraviolet radiation source in a disinfection illuminator that is used to irradiate a fuel nozzle for treatment purposes according to an embodiment.

FIG. 3 shows a more detailed view of an ultraviolet radiation source 32 in a disinfection illuminator that can be used to irradiate user contact surfaces. In one embodiment, the ultraviolet radiation source 32 depicted in FIG. 3 is suitable for use in the mounting station enclosure 30 depicted in FIG. 2, although those skilled in the art will appreciate that it is similarly applicable to use with other enclosures of disinfection illuminators described herein. In the embodiment illustrated in FIG. 3, the ultraviolet radiation source 32 can be configured in a housing 38 that is designed to focus ultraviolet illumination onto the surface of user contact sections (e.g., the handle 20 and/or the trigger 22 of a fuel nozzle in a gas station pump assembly) and prevent the ultraviolet radiation from spreading away from these surface sections. In one embodiment, the housing 38 can form a covering, a cap, a container, or the like for retaining an ultraviolet radiation source 32. With regard to a use with the mounting station enclosure 30 depicted in FIG. 2, the ultraviolet radiation source 32 and accompany housing 38 can be located on the internal surface of the mounting station enclosure in such a way that they along with any other sources and corresponding housings used to form the set of sources do not interfere with the fuel nozzle 18 being removed from and inserted into the mounting station 24 (FIG. 1A). Similarly, the set of ultraviolet radiation sources 32 and accompany housings 38 would not interfere with the set of sensors 34 and the control action 36, but instead would operate in conjunction with these components in the aforementioned manner.

In one embodiment, the housing 38 can include an inner wall surface having an ultraviolet reflective layer or coating formed on all or at least a portion thereof that facilitates recycling or recirculation of ultraviolet radiation that is emitted from the ultraviolet radiation sources 32. To this extent, the efficiency of a disinfection treatment applied to a user contact surface can be increased. An ultraviolet reflective layer or coating that is reflective to at least 30% and has a reflection coefficient of at least 50% will enable recycling of the ultraviolet radiation generation from the ultraviolet radiation sources 32. The ultraviolet reflective layer or coating can include a reflective material such as polished aluminum, a fluoropolymer, and/or a set of dielectric ultraviolet reflective and transparent layers.

In one embodiment, the ultraviolet reflective layer can include a diffusive ultraviolet reflective scattering layer. The diffusive ultraviolet reflective scattering layer can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

The ultraviolet radiation source 32 and housing 38 configuration depicted in FIG. 3, which is representative of an implementation with one of the enclosures for a disinfection illuminator of any of the various embodiments, can use an optical element to direct the ultraviolet radiation from the source onto a particular user contact surface (e.g., the handle and trigger of a fuel nozzle). Examples of optical elements that can be configured with the ultraviolet radiation source 32 and housing 38 can include, but are not limited to, lenses, mirrors, prisms and other reflective and light transmissive elements. Light guiding elements such as ultraviolet transparent elements with material like $Al_2O_3$, sapphire, $SiO_2$, $CaF_2$, $MgF_2$, or an ultraviolet transparent fluoropolymer are examples of other optical elements that can be used. In one embodiment, the optical elements can include an ultraviolet reflective media chosen from a group consisting of aluminum and an ultraviolet reflective fluoropolymer.

Figure 4:
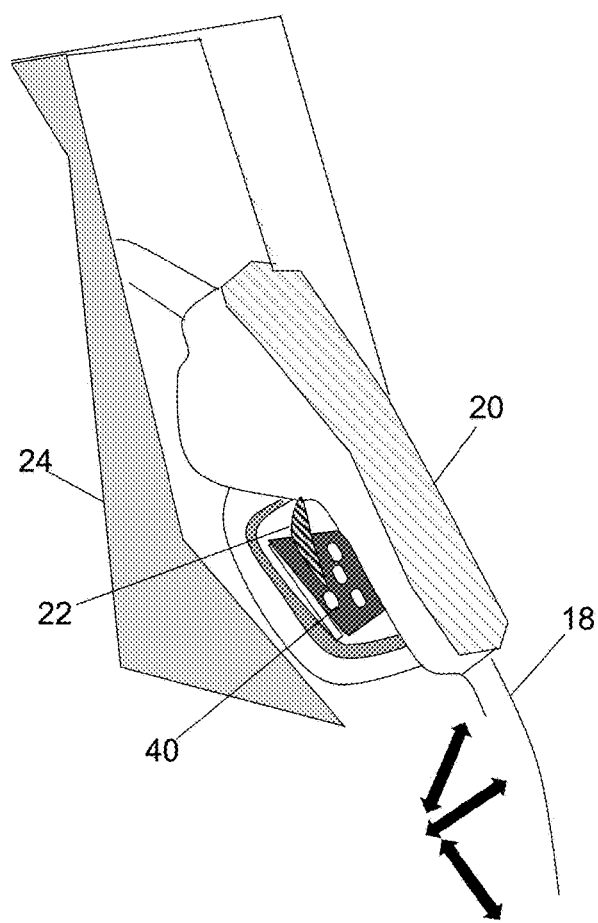
FIG. 4 shows a schematic view of a trigger disinfection component coupled to a mounting station in a gas station pump that is configured to irradiate the underside of the handle and the trigger of the fuel nozzle while the nozzle rests in the mounting station during a non-operational state according to an embodiment.

FIG. 4 shows a schematic view of a trigger disinfection component 40 coupled to a mounting station 24 in a gas station pump assembly unit 14 that is configured to irradiate the underside of the handle 20 and the trigger 22 of the fuel nozzle 18 while the nozzle rests in the mounting station during a non-operational state according to an embodiment. Although not specifically referenced in FIG. 4, the trigger disinfection component 40 can contain at least one ultraviolet radiation source 32 and sensor 34 as well as a control unit 36. In one embodiment, as shown in FIG. 4, the trigger disinfection component 40 can be positioned in the mounting station in a location that aligns underneath the trigger 22 and the underside of the handle 20 when the nozzle is resting in the mounting station 24. For gas station pump assemblies that have fuel dispensers of the type where the fuel nozzle sits in a holster tab that is moved up and down for initiating or completing the dispensing of gas, the trigger disinfection component 40 can be placed in the tab. In either configuration, the trigger disinfection component 40 is able to fully illuminate the surfaces of the trigger 22 as well as the underside of the handle that is typically gripped by a person while depressing on the trigger during the dispensing of fuel. It is understood that for an embodiment in which the fuel nozzle 18 resides in a mounting station 24 like that depicted in FIG. 4, the trigger disinfection component 40 can occupy an area within the mounting station 24 that is sufficient to account for the multi-directional movement that is allowed for the fuel nozzle 18 while resting in the station in a non-operational state as indicated by the arrows in the figure. This allows the trigger disinfection component 40 to provide an effective disinfection treatment no matter what position a user or operator of the fuel nozzle 18 returns the nozzle in the mounting station 24.

Figure 5:
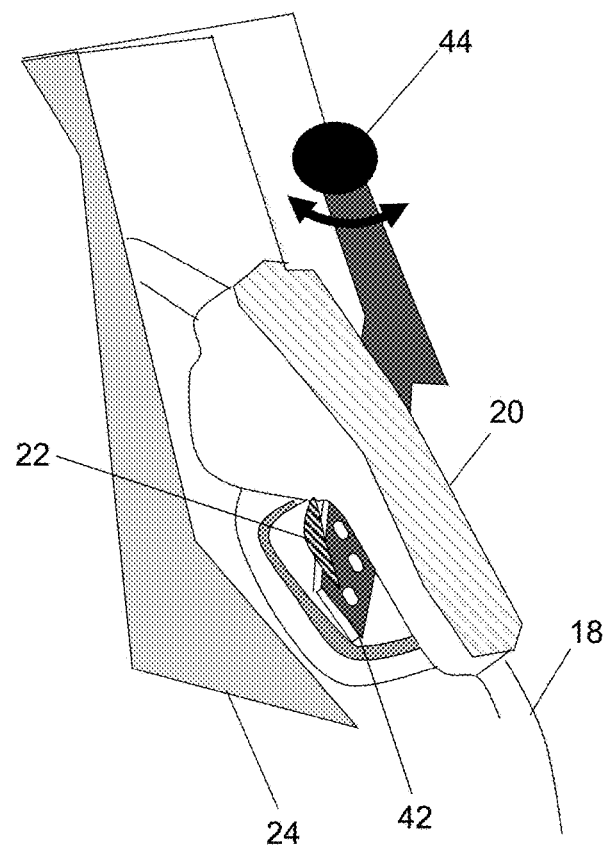
FIG. 5 shows a schematic view of a trigger disinfection component that is pivotably moveable from a first location that is adjacent the fuel nozzle to a second location that is underneath the handle and the trigger according to an embodiment.

FIG. 5 shows a schematic view of a trigger disinfection component 42 according to another embodiment that can be used to illuminate the surfaces of the trigger 22 and the underside of the handle 20. In this embodiment, the trigger disinfection component 42 can be positioned off to the side of the handle 20 and the trigger 22 while the fuel nozzle 18 rests in the mounting station 24 in a non-operational state. As shown in FIG. 5, a moveable joint 44 can be used to move the trigger disinfection component 42 in and out of two locations, with one location being where the trigger disinfection component is out of an irradiation coverage range of the trigger 22 and the surface of the underside of the handle 20 (e.g., it does not provide irradiation coverage of the trigger and handle for disinfection purposes), and another location allowing irradiation of the trigger 22 and the surface of the underside of the handle 20.

In one embodiment, the moveable joint 44 is a hinge that allows the trigger disinfection component 42 to be swiveled in out of the two locations as depicted by the movement of the arrows in FIG. 5. To this extent, the trigger disinfection component 42 can be pivotably moveable from a first location that is adjacent the handle 20 and the trigger 22 of the fuel nozzle 18, to a second location that is underneath the handle and the trigger that allows irradiation of these surfaces with a wider irradiation coverage.

Like the trigger disinfection component 40 depicted in FIG. 4, the trigger disinfection component 42 of FIG. 5 can contain at least one ultraviolet radiation source 32 and sensor 34 as well as a control unit 36. Further, it is understood that these components can operate in the aforementioned manner to effectuate a disinfection treatment of the handle 20 and the trigger 22 of the fuel nozzle 18.

FIG. 6 shows a schematic view of a disinfection illuminator 15 configured to disinfect the top side of the handle 20 of a fuel nozzle 18 and an underside of the nozzle including the trigger 22 while in the mounting station 24 during a non-operational state according to another embodiment. In this embodiment, the disinfection illuminator 15 can include a handle disinfection component 46 to illuminate the top side surface of the handle 20 and a trigger disinfection component 40 to irradiate the underside of the handle 20 and the trigger 22. The handle disinfection component 46 can include a set of ultraviolet radiation sources 32, a set of sensors 34 and a control unit 36, while the trigger disinfection component 40 could include these elements as noted above with regard to FIG. 4.

The ultraviolet radiation sources 32, the sensors 34 and the control unit 36 in both the handle disinfection component 46 and the trigger disinfection component 40 can operate in the same manner described above with regard to the general operation of the previously mentioned disinfection illuminators. For example, once it has been determined that the fuel nozzle 18 has been inserted into the mounting station 24 and is in a non-operational state, the control unit 36 of both the handle disinfection component 46 and the trigger disinfection component 40 can determine whether it is necessary to initiate a disinfection treatment of the upper side of the handle 20 and the trigger 22, and the underside of the handle, respectively. If only the control unit 36 of the trigger disinfection component 40 determines that the surfaces of the trigger 22 and the underside of the handle 20 have bacterial conditions exceeding a predetermined threshold, the control unit can instruct the radiation sources to irradiate the trigger and the underside of the handle to eradicate the proliferation of bacteria, viruses, pathogens, etc., that led to this determination. Similarly, it is possible that only the control unit 36 of the handle disinfection component 46 determines that the upper side of the handle contains bacterial conditions that need to be removed, and thus, will activate the ultraviolet radiation sources 32 to irradiate the upper side surfaces of the handle. It is understood, that there will be some instances after the fuel nozzle 18 has been replaced back in the mounting station 24 that neither the trigger disinfection component 40 nor the handle disinfection component 46 will determine that a disinfection treatment is necessary, and thus, no action is taken.

It is understood that the trigger disinfection component 40 and the handle disinfection component 46 can be implemented in other configurations than that depicted in FIG. 6. For example, the handle disinfection component 46 is shown in FIG. 6 as an overhang that extends generally over the upper portion of the fuel nozzle 18 including the upper side of the handle 20 once the nozzle is resting in the mounting station 24 in a non-operational state. In one embodiment, the handle disinfection component 46 can take the form of the enclosure 30 of the disinfection illuminator 13 depicted in FIG. 2, in which the enclosure substantially encloses the upper portion of the fuel nozzle 18 except at an open-ended bottom portion that is used for insertion and removal of the nozzle from the mounting station 24. Similarly, the trigger disinfection component 40 may take the form of the pivotably mounted version depicted in FIG. 5 in which the trigger disinfection component can be swiveled underneath the underside of the handle 20 to disinfect the trigger and underside handle surfaces, and removed from this position to one that is out of irradiation range but still adjacent to the handle to not interfere with its operation and removal from and insertion into the mounting station 24. It is also understood that the trigger disinfection component 40 and the handle disinfection component 46 can be configured without a control unit 36. For example, a control unit can be centrally located in a position on the gas station pump assembly or even be remote from the fuel dispenser in a location such as inside the store that has control over all of the fuel dispensers in a given station.

FIG. 7 shows a schematic view of a disinfection illuminator 17 that similar to the illuminator 13 depicted in FIG. 2, except that the disinfection illuminator 17 is shown having a coating or layer of material 48 on the internal surface to promote recycling of the ultraviolet radiation for improvement of the disinfection of the fuel nozzle 18 during a disinfection cleaning treatment according to an embodiment. In particular, the coating or layer of material 48 facilitates recycling or recirculation of ultraviolet radiation that is emitted from the ultraviolet radiation sources 32 in order to increase the efficiency of a disinfection treatment applied to the user contact surfaces of the handle 20 including the upper side and the underside of the handle, and the trigger 22. In one embodiment, the coating or layer of material 48 can be placed on the portion of the mounting station 24 that the handle 20 of the fuel nozzle 18 rests while in a non-operational state. It is understood that the coating or layer of material 48 can be placed on the internal under side of the enclosure 30 without interfering with the set of ultraviolet radiation sources 32 and the set of sensors 34. Although not shown in FIG. 7, the coating or layer of material 48 can be placed on a trigger disinfection component in manner that does not interfere with its ultraviolet radiation sources and sensors.

The coating or layer of material 48 can include a number of different reflective materials. For example, the coating or layer of material 48 can include an ultraviolet reflective material that is reflective to at least 30% and has a reflection coefficient of at least 50%. In one embodiment, the coating or layer of material 48 can include, but is not limited to, aluminum, expanding polytetrafluoroethylene (ePTFE) membrane (e.g., GORE® DRP® Diffuse Reflector Material), TEFLON, any of the aforementioned fluoropolymers, an omnidirectional mirror comprising a laminate of metallic and ultraviolet transparent and reflective dielectric layers, and/or the like. The coating or layer of material 48 can also include a diffusive ultraviolet reflective scattering layer having any of the aforementioned fluoropolymers.

Figure 8:
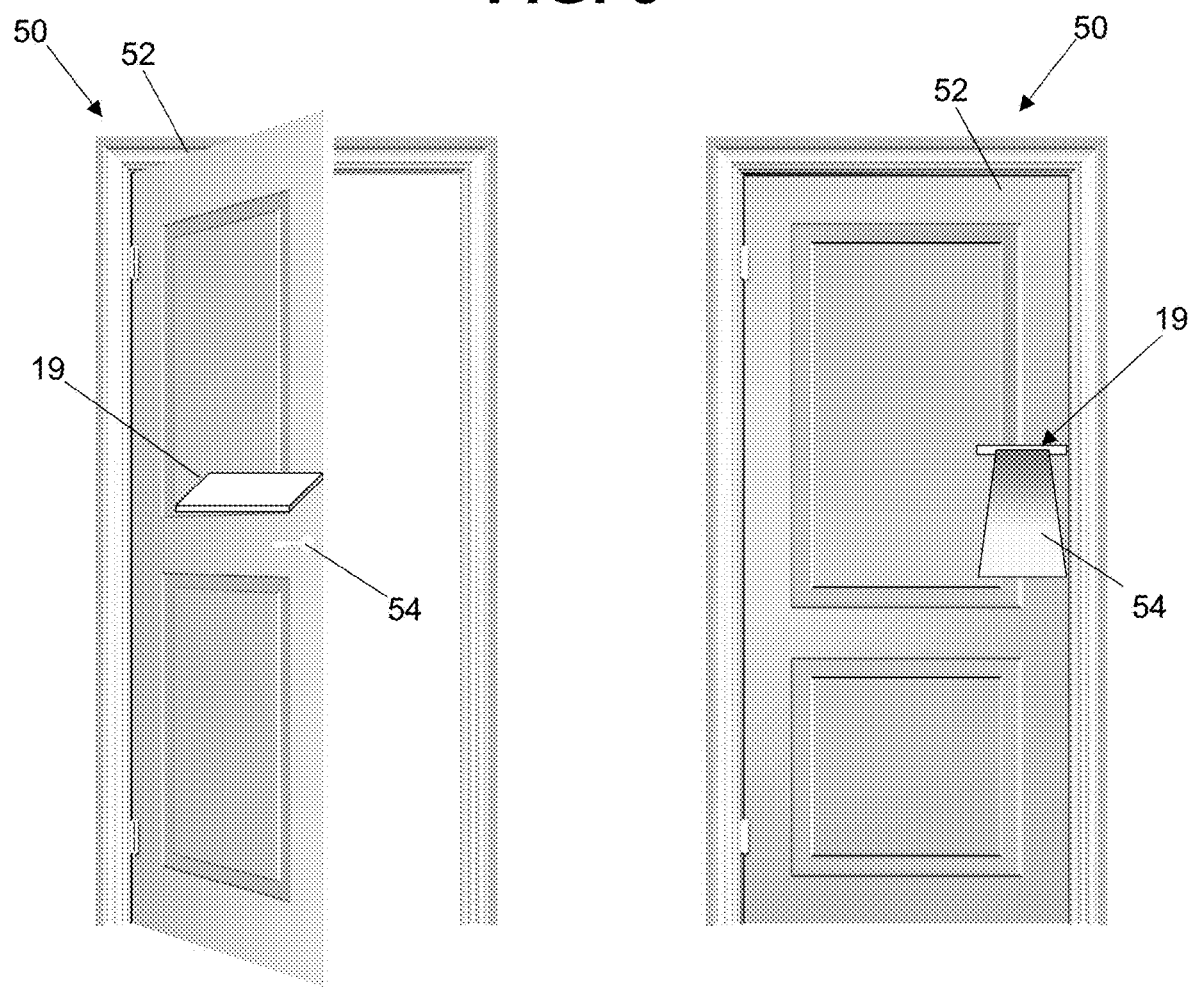
FIG. 8 shows a schematic of a system having a disinfection illuminator for treating a door having a door handle according to an embodiment.

A variation of the above-noted disinfection illuminators used for the disinfection of gas station pump assemblies can be used to treat door handles including door knobs and lever latch handles. FIG. 8 shows a schematic of a system 50 having a disinfection illuminator 19 for disinfecting a door 52 having a door handle 54 according to an embodiment. As shown in FIG. 8, the disinfection illuminator 19 can include an open-ended enclosure that is attachably secured to the door 52 about the door handle 54. In one embodiment, the enclosure that forms the disinfection illuminator 19 can be located above the door handle 54. It is understood that the enclosure can be positioned in other locations about the door handle such as above it, off to the side of the handle or in positions that encompasses above and below the handle. In any event, the enclosure of the disinfection illuminator 19 of FIG. 8 can be attachably secured to the door 52 about the door handle 54 using any fastener mechanisms described herein.

For clarity, the ultraviolet radiation sources 32, the sensors 34 and the control unit 36 discussed herein with respect to the disinfection illuminators used with the gas station pump assemblies are not shown in system 50 of FIG. 8, however, it is understood that these components would be included with the disinfection illuminator 19 of this embodiment. The ultraviolet radiation sources 32, the sensors 34 and the control unit 36 would operate in a similar manner, however, it is further understood that their operation would be tailored to the use of the door, the location of the door (e.g., the degree of public use that the door receives), the type of door handle that is used, the type of bacterial contamination conditions that are expected, and the like. For example, the disinfection illuminator 19 can be in a non-operational state when the door 52 is open (left-hand side of FIG. 8). Upon the shutting of the door (right-hand side of FIG. 8), the control unit of the disinfection illuminator 19 can determine whether the door handle 54 needs a disinfection treatment based on feedback from the set of sensors configured to ascertain the conditions (e.g., bacterial conditions) present on the handle. If the control unit determines that the door handle needs a disinfection treatment, then the control unit can activate the operation of the ultraviolet radiation sources to perform a disinfection treatment. The control unit can also monitor the disinfection treatment based on conditions detected by the sensors and adjust any operating parameters (e.g., intensity, duration, wavelength, etc.) of the sources in order to effectuate the treatment.

It is understood that there are many other modes of operating the disinfection illuminator 19 in the system 50 to facilitate a disinfection of the door handle 54. For example, the control unit of the disinfection illuminator 19 can initiate a disinfection based on a range of handle usage parameters such as the last time when the door handle 54 was used, the degree of bacterial contamination detected on the handle, and the visible aspects of surface contamination that are present on the handle. It is also understood that the input/output indicator that is part of the control unit as discussed above, can generate displays specific to the disinfection of the door 52 such as, but not limited to, the status of the disinfection process during the different stages such as the degree of contamination, types bacterial removed, the time left, etc.

Figure 9A:
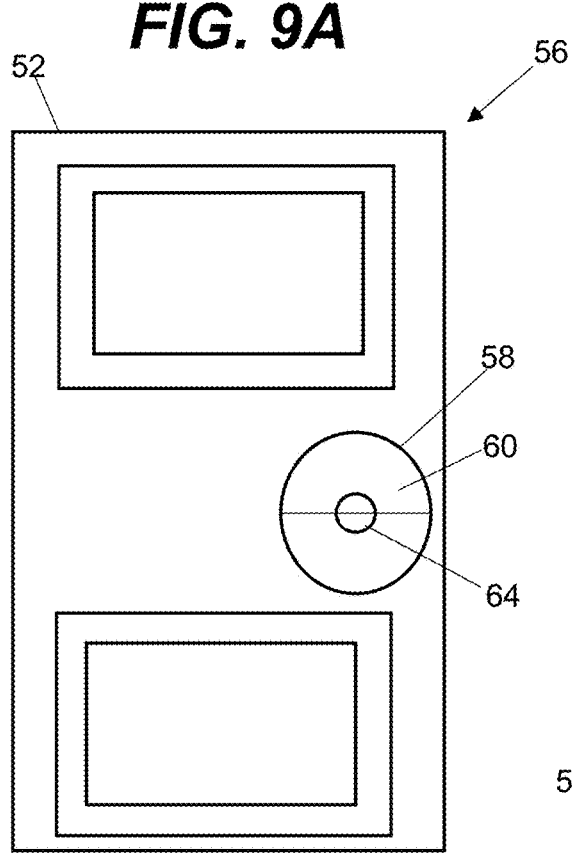
FIGS. 9A-9B shows a schematic of a system having a disinfection illuminator having an open-ended cylindrical housing having a cavity formed therein that is configured to encircle a door handle according to an embodiment.
Figure 9B:
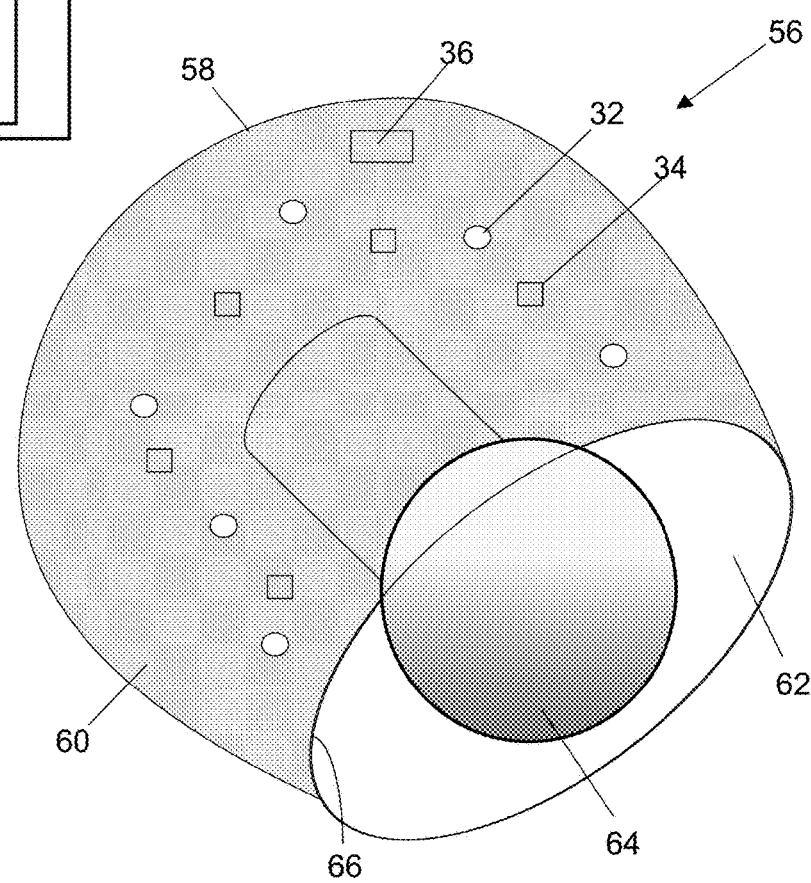

FIGS. 9A-9B shows a schematic of a system 56 having a disinfection illuminator 58 having an open-ended cylindrical housing 60 with a cavity 62 formed therein that is configured to encircle a door knob 64 of a door 52 according to an embodiment. As shown in FIG. 9B, the housing 60 of the disinfection illuminator 58 can include a set of ultraviolet radiation sources 32, a set of sensors 34 and a control unit 36. The ultraviolet radiation sources 32, the sensors 34 and the control unit 36 can operate in a manner described herein to effectuate a disinfection treatment of the door knob 64 (e.g., after closing of the door, per a set disinfection schedule, upon a user request to treat the door knob, or the like). It is understood that the location and types of the sources 32 and the sensors 34, as well as the operation of these components and the control unit 36 can be tailored to the aspect of disinfecting a door knob 64 with an open-ended housing that encircles the knob.

In one embodiment, the ultraviolet radiation sources 32, the sensors 34 and the control unit 36 can be positioned on an internal surface 66 of the housing 60. It is understood that the set of ultraviolet radiation sources 32 can be positioned on an exterior surface of the housing 60 with ultraviolet transparent windows formed on the surface to allow each of the sources to emit radiation into the housing to irradiate the door knob 64. Similarly, the control unit 36 can be positioned on the exterior of the housing 60, or parts of it can be distributed on both the internal and external surfaces of the housing. For example, the input/output component of the control unit 36 can be located on the exterior of the housing 60 in order to permit a user to input certain control parameters and/or receive various status information of the disinfection treatment.

It is understood that the open-ended housing 60 of this embodiment is not meant to be limited to a cylindrical shape. The cylindrical shape of the open-ended housing 60 of the embodiment depicted in FIGS. 9A-9B is used to correspond with a typical door knob having a cylindrical shape with an axis-symmetric body. Other housing shapes that correspond to different shaped door knobs are intended to be within the purview of this embodiment. Similarly, the cavity 62 of the open-ended cylindrical housing 60 with a circular entrance cross section depicted in FIGS. 9A-9B is not meant to be limiting to this embodiment as other cross-sectional shapes of the cavity 62 are within the scope this embodiment. Generally, the shape and size of the cavity 62 can be selected in a manner that makes it easy for hands of all sizes to fit in the cavity in order to open and close the door 52 and perform both locking and unlocking operations.

In one embodiment, the internal surface 66 of the housing 60 can have a coating or layer of material to promote recycling of the ultraviolet radiation for improvement of the disinfection of the door knob 64 during a disinfection treatment. For example, as noted above with regard to other embodiments, the coating or layer of material can include a number of different reflective materials such as the aforementioned ultraviolet reflective materials, fluoropolymers, and diffusive ultraviolet reflective scattering materials. Similarly, in another embodiment, the internal surface 66 of the housing 60 and/or the ultraviolet radiation sources 32 can be implemented with any of the aforementioned optical elements that direct the emitted radiation to specific surface portions of the door knob 64. It is understood that the coating or layer of material as well as the optical elements can be placed on the internal under-side of the housing without interfering with the set of ultraviolet radiation sources 32 and the set of sensors 34.

Figure 10A:
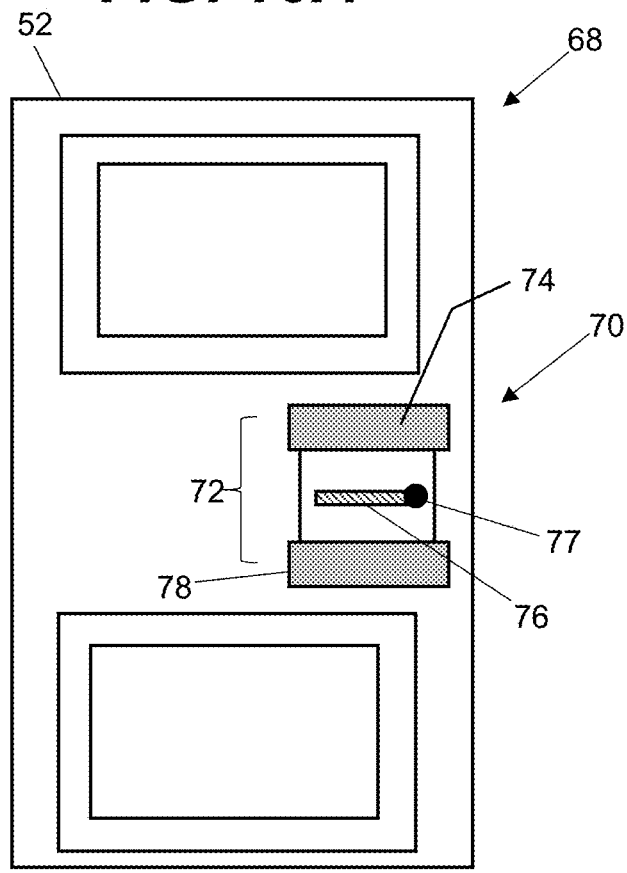
FIGS. 10A-10B shows a schematic of a disinfection illuminator for a door having a bi-level enclosure with a first enclosure level located above a door handle and a second enclosure level located underneath the handle, with two sets of handles each configured for rotation within the irradiation range of each enclosure level during a non-operation state according to an embodiment.
Figure 10B:
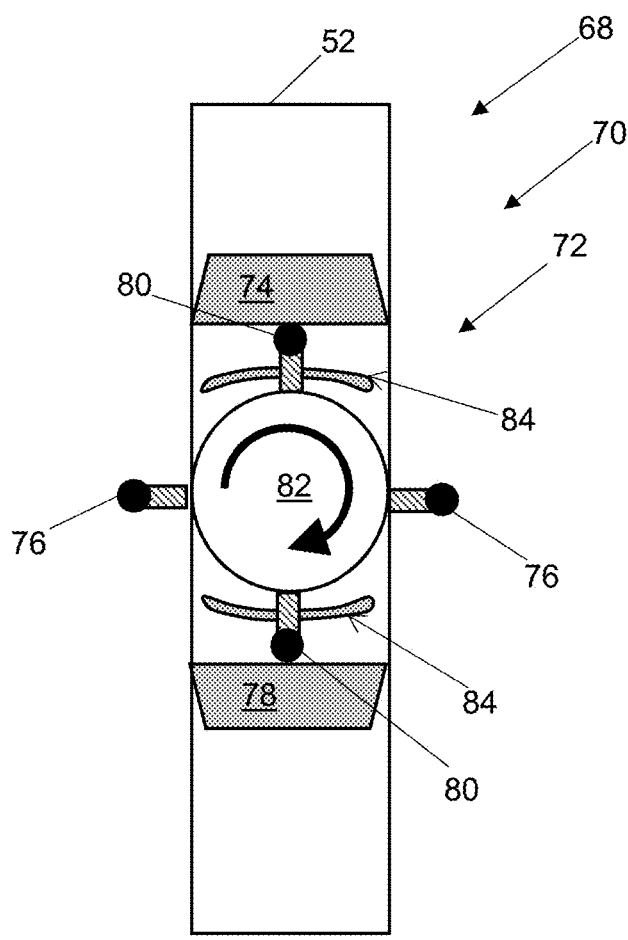

FIGS. 10A-10B show a schematic of a system 68 for disinfecting a door 52 with a disinfection illuminator 70 having a bi-level enclosure 72 with a first enclosure level 74 located above a door handle 76 and a second enclosure level 78 located underneath the handle. In particular, FIG. 10A shows a frontal view of the door 52 with the system 68, while FIG. 10B shows a cross-sectional view of the system with respect to the door. Although not shown in FIGS. 10A and 10B, the first enclosure level 74 and the second enclosure level 78 of the bi-level enclosure 72 can each include a set of ultraviolet radiation sources 32, a set of sensors 34 and a control unit 36. The ultraviolet radiation source 32, the sensors 34 and the control unit 36 can operate in conjunction with each other to effect a disinfection treatment the door handle 76. In one embodiment, the first enclosure level 74 can disinfect the top surface of the door handle 76, while the second enclosure level 78 can disinfect the bottom surface of the handle. It is understood that the ultraviolet radiation sources 32, sensors 34 and control unit 36 of the first enclosure level 74 and the second enclosure level 78 can effectuate a disinfection treatment on the door handle 76 in any of the approaches described herein. For example, once the door 52 has been shut, the control unit(s) of the first enclosure level 74 and the second enclosure level 78 can determine if any surface of the top or bottom portions of the door handle 76 has a sufficient level of bacterial conditions that warrant a disinfection treatment. The control unit(s) 36 can then initiate operation of any of the ultraviolet radiation sources to begin irradiating the door handle 76. The control unit(s) 36 can then monitor the disinfection and adjust any operating parameters as needed to properly disinfect the door handle. Like other embodiments discussed herein, a user can manually initiate a disinfection of the door handle with one or both of the first enclosure level 74 and the second enclosure level 78 depending on if the user wants to disinfect both sides of the door handle.

As shown in the cross-sectional view of FIG. 10B, the system 68 can further include the use of two sets of handles (76 and 80) with the door 52. In one embodiment, the door handles 76 and 80 can include a lever latch handle type as shown in FIGS. 10A-10B, however, it is understood that the bi-level enclosure 72 is suitable for use with other door handles such as door knobs. A rotating mechanism 82 can rotate each set of handles to a position that is within an irradiation range of both the first enclosure level 74 and the second enclosure level 78. For example, one set of the handles will always be in an operational state, i.e., operable to open and close the door 52 and be out of the irradiation range of the first enclosure level 74 and the second enclosure level 78. On the other hand, the other set of handles will be in a non-operational state, i.e., not operable to open and close the door 52, and be in the irradiation range of the first enclosure level 74 and the second enclosure level 78. In this manner, the sets of lever latch handles 76 and 80 are rotatable from a horizontal position that is used for opening and closing the door to a vertical position that is used for applying a disinfection treatment without having a capability to open and close the door. To this extent, one of the sets of the lever latch handles 76 and 80 is outside an irradiation coverage range of the first enclosure 74 and the second enclosure 78 while in the horizontal position, while the other set of handles is inside the irradiation coverage range of the first enclosure and the second enclosure while in the vertical position.

In one embodiment, the rotating mechanism 82 can include an electric motor. However, it is understood that other rotating mechanisms can be used to rotate the set of handles 76 and 80 in and out of the operational state (i.e., operable to open/close the door and not positioned for a disinfection by the first enclosure level 74 and the second enclosure level 78) to a non-operational state (i.e., positioned in a location for a disinfection by the first enclosure level 74 and the second enclosure level 78 and not operable to open/close door). Other examples of a rotating mechanism suitable for use with the embodiment depicted in FIGS. 10A and 10B can include, but are not limited to, a rotating mechanism operated by a spring that can be wounded by a motor, where the control mechanism releases the spring at a set time after the handle has been used. In an embodiment, the control mechanism can be accompanied with an alert, such as a sound and/or a light emission, to inform the user that the handle might disappear for a short period of time. While FIG. 10B shows an embodiment where the rotating unit 82 is cylindrical with circular cross-section. In an alternative embodiment, the rotating unit can comprise a cylinder with a rectangular cross-section.

In one embodiment, the control unit can operate the rotating mechanism 82 automatically by moving the set of handles 76 and 80 in out of the horizontal and vertical positions. For example, the control unit can detect when the handle was used, and engage rotating mechanism when the handle is not in use. To this extent, the rotating mechanism 82 ensures that the door 52 has one of the set of handles 76 and 80 in the horizontal position for opening and closing the door and the other set of handles in the vertical position ready for disinfection. The set of handles in the vertical position is configured for rotation by the rotating mechanism 82 to the horizontal position after disinfection for opening and closing the door 52. This permits the set of handles in the horizontal position to be moved to the vertical position for disinfection.

Figure 10C:
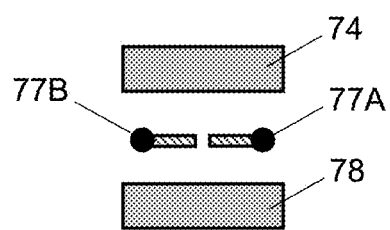
FIG. 10C shows an alternative configuration of a handle according to an embodiment.

The bi-level enclosure 72 can further include a pair of reflective surfaces 84 to increase the efficiency of the irradiation by recycling the radiation generated from the ultraviolet radiation sources 32 of the first enclosure level 74 and the second enclosure level 78. In one embodiment, one of the reflective surfaces 84 can be positioned underneath the first enclosure 74 and one of door handles from the set that happens to be in the vertical position ready for a disinfection, while the other reflective surface 84 can be positioned above the second enclosure 78 and the other door handle from the set in the vertical position. In one embodiment, the reflective surfaces 84 can the take the form of a flat or curved reflective surface. In an embodiment, the handle 76 is attached to the rotating mechanism 82 only at an end 77, with the opposing end hanging freely in the air. For such a configuration, surfaces 84 can be attached to an interior surface of the door. It is understood that other alternatives are possible, for example the handle 76 can have an opening in the middle as shown in FIG. 10C, with the opening used to allow support for the surfaces 84 using the opposing ends 77A, 77B. Alternatively, the end 77B can include a structure for supporting the surface 84, but not the handle 76. In this case, the handle 76 can extend up to or over the end 77B, but not be supported by the end 77B. It is also understood that the pair of reflective surfaces 84 can be configured in other positions located about the door handles and the first enclosure 74 and the second enclosure 78. Further is understood, that the reflective surfaces 84 can have any of the aforementioned coatings or layers of ultraviolet reflective materials that can promote the recycling of ultraviolet radiation.

Figure 11:
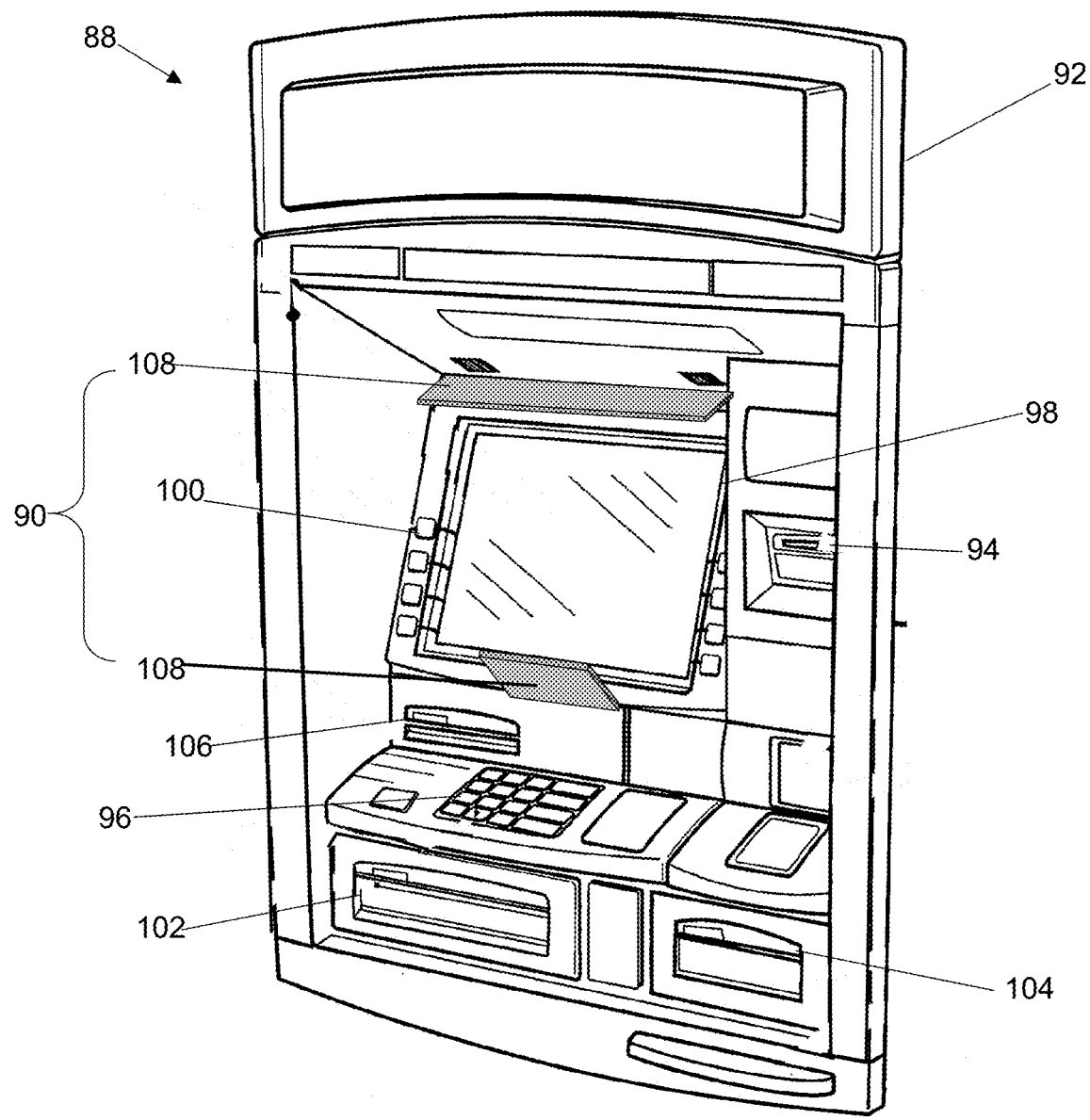
FIG. 11 shows a schematic of a system having disinfection illuminators for treating a user-interactive transaction device having user interactive components that require user contact to facilitate an aspect of a transaction, such as for example an automatic teller machine, according to an embodiment.

FIG. 11 shows a schematic of a system 88 having a disinfection surface treatment unit 90 for disinfecting a user-interactive transaction device having user interactive components that require user contact to facilitate an aspect of a transaction according to an embodiment. In the embodiment depicted in FIG. 11, the user-interactive transaction device is an automatic teller machine (ATM) 92. It is understood that the system 88 is applicable to any user-interactive transaction device having a multitude of surfaces that are subject to on-going contact with the general public and that can become contaminated with a plethora of pathogens such as microbes, bacteria, fungi and the like that are highly associated with illness and disease that can wreak havoc on a person's health. As used herein, a user-interactive transaction device is any device, machine, equipment or fixture that has a number of user-interactive input and output components (e.g., selector buttons, keypads, touch screens, drawers, slots, handles, writing devices, knobs, printers, displays, speakers, and the like) that require user interaction therewith through any degree of contact with a surface of the components in order to facilitate a transaction of exchanging goods, services and financial instruments. Examples of other user-interactive transaction devices that are suitable for use with the disinfection surface treatment unit 90 include, but are not limited, to point of sale devices (e.g., cash registers, scanners, scales), parking meters, kiosks having user-interactive screens and displays, entrance and exit gates having user-interactive screens and displays for entering and exiting locations, toll booths, etc.

As shown in FIG. 11, the ATM 92 can include a variety of user interactive components each requiring user contact in order to facilitate an aspect of a transaction. For example, a card reader 94 captures the account information stored on the magnetic stripe on the back of an ATM/debit or credit card that is fed in by a cardholder or user of the ATM 92. A keypad 96 and a display 98 let the user tell a bank what kind of transaction is desired (e.g., cash withdrawal, balance inquiry, etc.) and for what amount after the user has entered his or her personal identification number (PIN) for verification. Other components of the ATM 92 can include screen buttons 100 that facilitate user inputs to queries presented in the display 98, a cash dispenser 102 that dispenses cash to the user upon validation of the transaction by the bank, a deposit slot 104 that can receive deposits from the user, and a printer 106 that can print out a receipt of the transaction for the user.

The surface treatment unit 90 can include a plurality of disinfection illuminators 108 with each configured to irradiate one of the user interactive components of the ATM 92 with ultraviolet radiation. For example, FIG. 11 shows that the disinfection surface treatment unit 90 can include a disinfection illuminator 108 located about the keypad 96 and another illuminator located about the display 98. In one embodiment, the disinfection illuminators 108 are located above the keypad 96 and the display 98. It is understood that the disinfection illuminators 108 can be located in other positions with respect to the keypad 96 and the display 98. For example, these disinfection illuminators 108 can be located off to a side or bottom of the keypad 96 and the display 98. Also, it is understood that the disinfection surface treatment unit 90 can include other disinfection illuminators 108 located about other user interactive components of the ATM 92 such as for example, the buttons 100, the cash dispenser 102, the deposit slot 104, and the printer 106.

In one embodiment, the disinfection illuminators 108 can take the form of coverings or overhangs that are secured to the ATM 92. For example, each of the coverings can be secured to any of the user-interactive components (e.g., the keypad 96, the display 98, the buttons 100, the cash dispenser 102, the deposit slot 104, and the printer 106) of the ATM 92 by using any of the fastener mechanisms described herein. It is understood that the disinfection illuminators 108 are not meant to be limited to coverings or overhangs but instead can be implemented in other configurations such as any of the open-side enclosures described herein.

As with the disinfection illuminators of the other embodiments, each of the disinfection illuminators 108 in FIG. 11 can include, although not illustrated, a set of ultrasound radiation sources 32, a set of sensors 34 and a control unit 36 that operate in conjunction to disinfect contact surfaces associated with the user-interactive components. For example, the sensors 32 can be used to detect the conditions (e.g., bacterial conditions) present at the surfaces of the various user-interactive components and send signals representative of the conditions to the control units 36. Each respective control unit 36 can monitor the conditions and determine if the signals are indicative of conditions that are sufficient to warrant a disinfection treatment. The control unit 36 can activate operation of at least one the ultraviolet sources in its respective enclosure upon determining that the contact surfaces of the user interactive component that it is tasked to irradiate is in need of a disinfection treatment. The activating can include specifying any of the aforementioned operating parameters for the disinfection treatment such as the cleaning treatment time, the dosage of ultraviolet radiation delivered, the power setting of the ultraviolet radiation sources, and the maximum operating temperature of the treatment. These operating parameters can also be adjusted by the control unit depending on conditions detected by the sensors. In addition, a user could manually enter certain operating conditions through the input/output component of the control unit 36 to effectuate a particular type of disinfection treatment.

It is understood that the disinfection illuminators 108 could be implemented with other features that can enhance the disinfection treatment of any of the user interactive components of the ATM 92. For example, the disinfection illuminators 108 and/or the surfaces of the corresponding user interactive components can be implemented with any of the aforementioned ultraviolet reflective surfaces that can increase the efficiency and recycling of the ultraviolet radiation generated from the ultraviolet radiation sources. In addition, the ultraviolet radiation sources 32 can be configured with any of the previously mentioned optical elements to focus the emitted radiation to specific locations along surfaces of the user interactive components.

Also, it is understood that although the disinfection illuminators 108 are described as each having a control unit that controls the operation of its respective ultraviolet radiation sources 32 and sensors 34, the system 88 can utilize a centralized control unit that controls the operation of the sources and sensors in each of the illuminators. For example, the centralized control unit can be located in another location within the ATM 92 or at a remote location such as within the bank or establishment in which the ATM operates.

Figure 12:
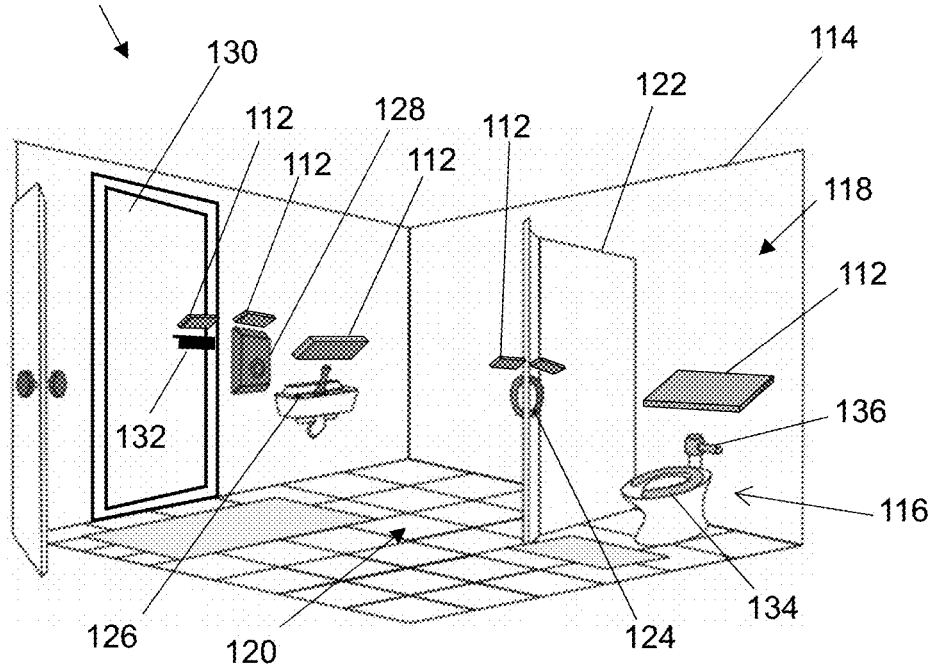
FIG. 12 shows a schematic of a system having disinfection illuminators for treating various contact surfaces in a public room according to an embodiment.

FIG. 12 shows a schematic of a system 110 having disinfection illuminators 112 for disinfecting various contact surfaces in a public room 114 according to an embodiment. In the embodiment depicted in FIG. 12, the public room 114 is a public bathroom. It is understood that the system 110 is applicable to any room available to the general public having a high number of people entering and leaving the room, where there is frequent contact of a multiple of commonly-used surfaces by these people while in the room. As a result, these commonly-used surfaces can become contaminated with pathogens such as microbes, bacteria, fungi, and the like, that are highly associated with illness and disease and that can be passed onto a person through contact with the surfaces. Examples of other public rooms that are suitable for use with the system 110 and the disinfection illuminators include, but are not limited, to escalators, trains, planes, buses, malls, restaurants, etc.

As shown in FIG. 12, the public bathroom 114 can include a variety of plumbing fixtures and hygienic devices in addition to other fixtures such as light switches and doors. In FIG. 12, the public bathroom 114 includes a toilet 116 in a stall 118 separated from a wash area 120 by door 122 having a handle 124 on both sides of the door. The wash area 120 can include a sink 126, a hand dryer 128 and an entrance/exit door 130 and handle 132 enabling ingress to and egress from the bathroom 114. It is understood that the public bathroom 114 depicted in FIG. 12 is only an example of one possible configuration and is not meant to limit the scope of the system 110 and the disinfection illuminators 112. For example, the bathroom 114 could be configured with other hygienic devices such as, paper towel dispensers, garbage cans, air fresheners and at other locations having contact surfaces with higher incidences of human interaction that are subject to bacterial contamination. The system 110 and the disinfection illuminators 112 of this embodiment are suitable for use with other bathrooms configured to include more or less of the plumbing fixtures, hygienic devices and other basic fixtures depicted in FIG. 12.

Like the aforementioned disinfection illuminators of the other embodiments described herein, each of the disinfection illuminators 112 in FIG. 12 can include, although not illustrated, a set of ultrasound radiation sources 32, a set of sensors 34 and a control unit 36 that operate in conjunction with each other to disinfect contact surfaces associated with a specific location in the bathroom 114. In one embodiment, disinfection illuminators 112 can be located about the toilet 116, the handles 124 of the door 122 into the stall 118, the handle 132 of the door 130 leading into the wash area 120 of the bathroom 114, the sink 126 and the hand dryer 128. To this extent, the disinfection illuminator 112 located about the toilet 116 can disinfect a toilet seat 134 and a toilet handle 136, the disinfection illuminator 112 located about the door 122 can disinfect the handles 124, the disinfection illuminator 112 located about the door 130 can disinfect the handle 132, the disinfection illuminator 112 located about the sink 126 can disinfect the sink, and the disinfection illuminator 112 located about the hand dryer 128 can disinfect the hand dryer. It is noted that each of these disinfection illuminators 112 generally have an operational range that extends a predetermined distance about the fixture that it is designated to operate with.

In operation, the set of sensors 32 associated with the corresponding disinfection illuminators 112 can be used to detect the conditions (e.g., bacterial conditions) present at the surfaces of the toilet seat 134, the toilet handle 136, the handles 124, and the handle 132, and send signals representative of the conditions to control unit(s) 36. Each respective control unit 36 can monitor the conditions and determine if the signals are indicative of bacterial conditions that are sufficient to warrant a disinfection treatment. The control unit 36 can activate operation of at least one of the ultraviolet sources in its respective disinfection illuminator 112 upon determining that the contact surfaces that it is designated to irradiate is in need of a disinfection treatment. The activating can include specifying any of the aforementioned operating parameters for the disinfection treatment such as the disinfecting treatment time, the dosage of ultraviolet radiation delivered, the power setting of the ultraviolet radiation sources, and the maximum operating temperature of the treatment. These operating parameters can also be adjusted by the control unit depending on conditions detected by the sensors. In addition, a user could manually enter certain operating conditions through the input/output component of the control unit 36 to effectuate a particular type of disinfection treatment. For example, an individual entering the stall 118 could manually instruct the control unit associated with the disinfection illuminator 112 located above the toilet 116 to conduct a disinfection treatment of the toilet before using it.

It is understood that the disinfection illuminators 112 could be implemented with other features that can enhance the disinfection treatment of any of the contact surfaces in the bathroom 114. For example, the disinfection illuminators 112 and/or the surfaces of the fixtures can be implemented with any of the aforementioned ultraviolet reflective surfaces that can increase the efficiency and recycling of the ultraviolet radiation generated from the ultraviolet radiation sources. In addition, the ultraviolet radiation sources 32 can be configured with any of the previously mentioned optical elements to focus the emitted radiation to specific locations along any of the various contact surfaces that are commonly used in the bathroom 114.

Although the disinfection illuminators 108 are described as each having a control unit that controls the operation of its respective ultraviolet radiation sources 32 and sensors 34, the system 110 can utilize a centralized control unit that controls the operation of the sources and sensors in each of the illuminators 112. For example, in one embodiment the centralized control unit can be located in one location within the wash area 120 of the bathroom 114, or in another location remote from the bathroom.

In one embodiment, each of the disinfection illuminators 112 can be operatively coupled with each other and operated based on human actions and/or inactions occurring in the locations within an operational range of the disinfection illuminators. That is, the disinfection illuminators 120 can be connected to each other and be activated depending on what surfaces a user touched or did not touch while in the bathroom 114. For example, if the user touched the toilet handle 136, but did not use the sink 126 to wash his or her hands, then a centralized control unit can instruct the disinfection illuminator 112 above the handle 132 of the door 130 to be activated to disinfect that handle. In another example, in a scenario in which the bathroom is situated in a public establishment such as a restaurant, a bar, a coffee shop, a hospital, etc., the control unit can have an output such as a speaker, a light, a display, or the like, to remind employees and/or patrons to wash their hands in the sink 126 after using the toilet 116 and touching the toilet seat 134 and handle 136. It is understood that the types of warnings, notifications, and the like that can be generated are boundless, and thus, this embodiment is not meant to be limited to any particular type of output.

In yet another example, the control unit can generate an output to the employees and/or patrons if the operatively coupled disinfection illuminators 112 detect that the person is about to exit the bathroom 114 through the door 130 turning the handle 132 without having used the sink 126 and the dryer 128. If an employee chooses to ignore the warning, recommendation, or the like to wash his or her hands, the control unit can activate the appropriate disinfection illuminators 112 to disinfect the fixture(s) susceptible to bacterial contamination build-up through that person's inaction. In one embodiment, the control unit can be configured to notify a manager of the establishment of the failure of the employee to practice proper lack hygiene.

These examples illustrate only a few possibilities in which the communicating disinfection illuminators 112 can be used to disinfect fixtures in a public bathroom. It is understood that the operatively coupled disinfection illuminators 112 can be used in a number of other implementations that efficiently disinfect the user contact surfaces of the bathroom 114 by detecting the presence of bacterial contamination through the use of sensors in the illuminators and eradicating the contamination with the ultraviolet radiation. For instance, the system 110 of disinfection illuminators 112 can determine that a particular area in the bathroom or fixtures is contaminated beyond the capability of the illuminators. In this scenario, the control unit can contact a HAZMAT team to come and clean that particular area of the bathroom. In addition, the control unit can generate a warning to people entering the bathroom 114 that there is an extremely high level of contamination, and that they should refrain being near the specific area with this level of contamination.

In addition, the centralized control unit can be used in other capacities beyond the general monitoring and controlling of the ultraviolet radiation sources and sensors during a disinfection treatment. For example, the control unit can compile statistical data pertaining to fixtures that have a higher percentage of bacterial contamination and the historical data that has been used to eradicate the build-up of bacterial conditions in the bathroom 114. In one embodiment, the control unit can collect, store and process the statistical data on the frequency usage of the various doors, toilet and sink handle fixtures in the bathroom and the historical values of radiation wavelength, dosage, intensity and power that effectuated a proper disinfection treatment of these fixtures.

Figure 13:
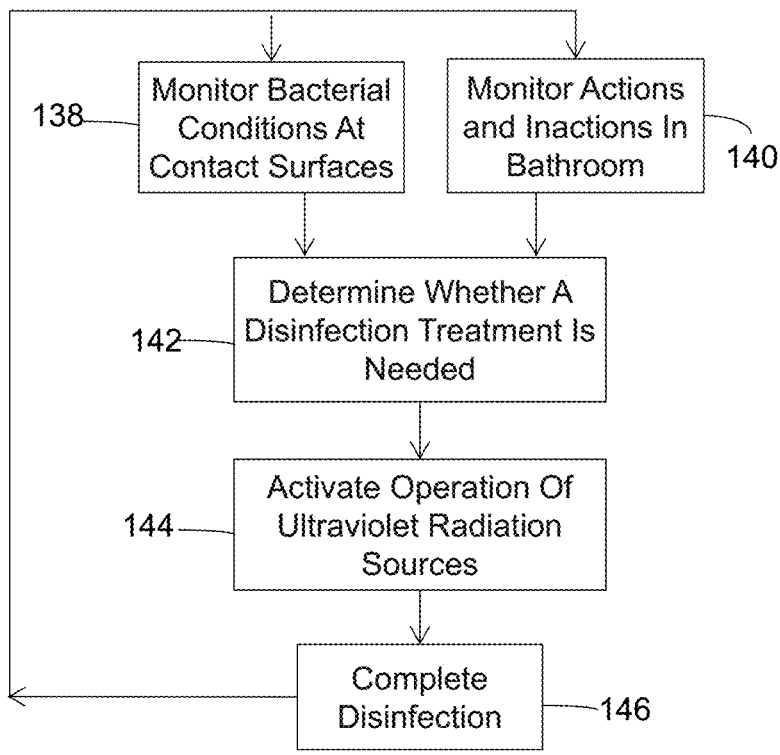
FIG. 13 shows a schematic of a flow chart illustrating examples of actions that can be performed by the disinfection illuminators of the system depicted in FIG. 12 during a treatment according to an embodiment.

FIG. 13 shows a schematic of a flow chart illustrating examples of actions that can be performed by the system 110 depicted in FIG. 12 in the disinfection of the public bathroom 114 according to an embodiment. In the flow chart of FIG. 13, the process can begin at 138 where a central control unit monitors bacterial conditions at the various contact surfaces associated with the fixtures in the bathroom 114 that each disinfection illuminator 112 is assigned for disinfection coverage. This can include the control unit receiving feedback from the sensors in each of the disinfection illuminators 112 on the level and type of bacterial conditions present surfaces. In addition, the control unit can simultaneously monitor the actions and/or inactions of each human entering and exiting the bathroom 114 at 140. In particular, the control unit can receive feedback from the sensors in each of the disinfection illuminators 112 on the actions taken in the bathroom 114 such as using the toilet 116, touching the door handles 122, and inactions that occurred such as failing to use the sink 126 and dryer 128 to wash and dry their hands.

The control unit can use the feedback from the sensors of the various disinfection illuminators at 142 to determine whether any of the contact surfaces need a disinfection treatment based on feedback of the conditions at the contact surfaces and the actions and/or inactions by each person entering and leaving the public room. The control unit can then activate operation of the ultraviolet radiation sources in any of the disinfection illuminators at 144 based on the occurrence of a predetermined amount of actions or inactions and/or detection of bacterial contamination conditions. The activating can include specifying a plurality of operating parameters for performing the disinfection treatment of the contact surfaces. The operating parameters can include, but are not limited to, a cleaning treatment time that the ultraviolet radiation sources emit ultraviolet radiation towards the contact surfaces, a dosage of ultraviolet radiation delivered by the ultraviolet radiation sources, a power setting for operating the ultraviolet radiation sources, and a maximum operating temperature for the disinfection.

The control unit can then monitor the disinfection process, make any adjustments to the parameters, generate any notifications and/or warnings to people entering and leaving the bathroom at 146, and complete the disinfection at 148. In this manner, the control unit can facilitate a disinfection treatment of the contact surfaces in the bathroom 114 that are in an irradiation range of coverage of each of the activated disinfection illuminators 112 to remove any bacterial contamination conditions. The control unit can then can continue to monitor conditions and the actions/inactions taken by those entering and leaving the bathroom.

It is understood that all of the various embodiments described herein can be implemented with a number of other modalities that will enhance or improve the disinfection of user contact surfaces that is performed by all of the disinfection illuminators in these embodiments. For example, to minimize the spreading of germs over the user contact surfaces, these surfaces can be treated with dry air to avoid proliferation of micro-organisms in a damp humid environment. In another embodiment, the surfaces can be treated with heated air to eliminate microorganisms. In one embodiment, the user contact surfaces can be treated with disinfectant chemical agents through the use of chemical sprays and gases such as ozone. In an embodiment, the user contact surfaces can have photoactive materials applied that can eliminate bacteria when exposed to ultraviolet light. A non-limiting example of a photoactive material can include, but is not limited to, $TiO_2$.

FIG. 14 shows a schematic block diagram representative of an overall processing architecture 800 according to an embodiment that is applicable to any of the systems described herein that include any of the disinfection illuminators described herein that utilize the ultraviolet radiation source(s) 32, the sensor(s) 34 and the control unit 36. As depicted in FIG. 14, the control unit 128 can be implemented as a computer system 820 including an analysis program 830, which makes the computer system 820 operable to manage the ultraviolet radiation source(s) 32 and the sensor(s) 34 in the manner described herein. In particular, the analysis program 830 can enable the computer system 820 to operate the ultraviolet radiation source(s) 32 to generate and direct ultraviolet radiation towards a user contact surface and process data corresponding to one or more attributes, which can be acquired by the sensor(s) 34, and/or an ultraviolet radiation history stored as treatment data 840. The computer system 820 can individually control each ultraviolet radiation source 32 and sensor 34 and/or control two or more of the ultraviolet radiation sources and the sensors as a group. Furthermore, the ultraviolet radiation source(s) 32 can emit ultraviolet radiation of substantially the same wavelength or of multiple distinct wavelengths.

In an embodiment, during an initial period of operation, the computer system 820 can acquire data from at least one of the sensor(s) 34 regarding one or more attributes of a surface and surface environment, and generate data 840 for further processing. The data 840 can include information regarding a presence of biological activity (e.g., microorganisms, viruses, bacteria, and/or the like) on a surface, a frequency of usage or contact of that surface, a disinfection schedule history for the environment, an amount of radiation (e.g., ultraviolet, infrared, visible, and/or microwave) detected, and/or the like. The computer system 820 can use the data 840 to control one or more aspects of the ultraviolet radiation generated by the ultraviolet radiation source(s) 32 during a disinfection treatment.

Furthermore, one or more aspects of the operation of the ultraviolet radiation source(s) 32 can be controlled or adjusted by a user 812 via an external interface I/O component 826B. The external interface I/O component 826B can be located on the exterior of any of the aforementioned disinfection illuminators, and used to allow the user 812 to selectively turn on/off the ultraviolet radiation source(s) 32.

The external interface I/O component 826B can include, for example, a touch screen that can selectively display user interface controls, such as control dials, which can enable the user 812 to adjust one or more of: an intensity, scheduling, and/or other operational properties of the set of ultraviolet radiation source(s) 32 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of ultraviolet radiation source(s) 32. The external interface I/O component 826B also can include any combination of various output devices (e.g., an LED, a visual display), which can be operated by the computer system 820 to provide status information pertaining to a disinfection treatment for use by the user 812. For example, the external interface I/O component 826B can include one or more LEDs for emitting a visual light for the user 812, e.g., to indicate a status of the cleaning treatment. In an embodiment, the external interface I/O component 826B can include a speaker for providing an alarm (e.g., an auditory signal), e.g., for signaling that ultraviolet radiation is being generated or that a cleaning treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the cleaning treatment. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 14 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system for treating a fixture having at least one hand-operated device, comprising:
    a surface treatment unit configured to irradiate the at least one hand-operated device, the surface treatment unit including at least one disinfection illuminator having a covering coupled to the at least one hand-operated device, the covering including at least one ultraviolet radiation source that is configured to emit ultraviolet radiation towards user contact surfaces associated with the at least one hand-operated device, and at least one sensor configured to detect bacterial conditions at the user contact surfaces; and a control unit, operatively coupled to the surface treatment unit, that monitors bacterial conditions at the user contact surfaces of the at least one hand-operated device through feedback provided by the at least one sensor and determines whether any of the user contact surfaces of the at least one hand-operated device need a treatment based on at least one of: the feedback of the bacterial conditions at the user contact surfaces or an operational state of the at least one hand-operated device, the control unit activating operation of the at least one ultraviolet radiation source in response to determining that at least a portion of the user contact surfaces of the hand-operated device needs a treatment, wherein the activating includes specifying a plurality of operating parameters for the treatment, the plurality of operating parameters including a treatment time that the at least one ultraviolet radiation source emits the ultraviolet radiation towards the user contact surfaces, a dosage of ultraviolet radiation delivered by the at least one ultraviolet radiation source, a power setting for operating the at least one ultraviolet radiation source, and a maximum operating temperature for the treatment.

2. The system of claim 1, wherein the control unit comprises an input component that permits a user to adjust at least one of the plurality of operating parameters, and an output component that generates status information of the treatment that is indicative of a treatment status at any of the user contact surfaces of the at least one hand-operated device.

3. The system of claim 1, wherein an internal surface of the covering comprises a coating or layer of one of a reflective material, an ultraviolet reflective material, and a diffusive reflective scattering material.

4. The system of claim 1, wherein the fixture having the at least one hand-operated device includes at least one of a gas station pump, a door, an automatic teller machine or a bathroom fixture.

5. A system, comprising:
a door having a door handle on at least one side of the door for opening and closing the door;
a user-interactive device, operatively coupled to the door, the user-interactive device having a plurality of user interactive components requiring user contact therewith to facilitate the opening and closing of the door;
a surface treatment unit including at least one disinfection illuminator configured to irradiate the plurality of user interactive components and the door handle with ultraviolet radiation, the at least one disinfection illuminator including an open-ended enclosure that is attachably secured to the door about the door handle and the plurality of user interactive components, at least one ultraviolet radiation source integrated with the enclosure that is configured to emit ultraviolet radiation towards the door handle and the plurality of user interactive components and a control unit operatively coupled to the door and the user interactive device, the control unit configured to control the ultraviolet irradiation of the plurality of user interactive components and the door handle, wherein the control unit determines whether at least one of the door handle and the plurality of user interactive components needs a treatment, the control unit activating operation of the at least one ultraviolet source in response to determining that the at least one of the door handle and the plurality of user interactive components needs a treatment, wherein the activating includes specifying a plurality of operating parameters for the treatment, the plurality of operating parameters including a treatment time that the at least one ultraviolet radiation source emits the ultraviolet radiation towards at least one of the door handle and the plurality of user interactive components, a dosage of ultraviolet radiation delivered by the at least one ultraviolet radiation source, a power setting for operating the at least one ultraviolet radiation source, and a maximum operating temperature for the treatment.

6. The system of claim 5, wherein the at least one disinfection illuminator further includes at least one sensor configured to monitor conditions at the user contact surfaces.

7. The system of claim 6, wherein the at least one sensor comprises a plurality of sensors each configured to monitor a predetermined condition at the user contact surfaces, the plurality of sensors comprising at least one of: a visible sensor, an infrared sensor, a bacterial fluorescent sensor, a chemical sensor, a radiation sensor, a pressure sensor, a temperature sensor, a humidity sensor, or a motion detector.

8. The system of claim 5, wherein the control unit is configured to perform operations that include:
monitoring conditions at the user contact surfaces of the plurality of user interactive components and the door handle;
determining whether any of the user contact surfaces of the plurality of user interactive components and the door handle need a treatment based on the conditions at the user contact surfaces; and
activating operation of the at least one ultraviolet radiation source to treat the user contact surfaces of any of the user interactive components and the door handle that have bacterial contamination.

9. The system of claim 5, wherein the enclosure comprises an internal surface having a coating or layer of one of: a reflective material, an ultraviolet reflective material, or a diffusive reflective scattering material.

10. The system of claim 5, wherein the at least one ultraviolet radiation source comprises a plurality of ultraviolet light emitting devices.

11. The system of claim 5, wherein the at least one disinfection illuminator includes a first disinfection illuminator located about the plurality of user interactive components and a second disinfection illuminator located about the door handle.

12. The system of claim 5, wherein the at least one ultraviolet radiation source is configured to operate at a wavelength that ranges from about 200 nanometers (nm) to about 310 nm.

13. A system, comprising:
a door having a door handle on at least one side of the door for opening and closing the door;
a disinfection illuminator configured to irradiate the door handle with ultraviolet radiation, the disinfection illuminator including an open-ended enclosure that is attachably secured to the door about the door handle, at least one ultraviolet radiation source integrated with the enclosure that is configured to emit ultraviolet radiation towards the door handle, and a control unit that determines whether the door handle needs a treatment, the control unit activating operation of the at least one ultraviolet source in response to determining that the door handle needs a treatment, wherein the activating includes specifying a plurality of operating parameters for the treatment, the plurality of operating parameters including a treatment time that the at least one ultraviolet radiation source emits the ultraviolet radiation towards the door handle, a dosage of ultraviolet radiation delivered by the at least one ultraviolet radiation source, a power setting for operating the at least one ultraviolet radiation source, and a maximum operating temperature for the treatment.

14. The system of claim 13, wherein the disinfection illuminator further comprises at least one sensor configured to monitor the treatment of the door handle and provide signals thereof to the control unit, the at least one sensor selected from the group consisting of: a visible sensor, an infrared sensor, a bacterial fluorescent sensor, a chemical sensor, a radiation sensor, a pressure sensor, a temperature sensor, a humidity sensor, a motion detector, and combinations thereof.

15. The system of claim 13, wherein the door handle comprises a door knob, wherein the enclosure comprises an open-ended cylindrical housing having a cavity formed therein that is configured to encircle the door knob, and wherein the cylindrical housing includes a plurality of ultraviolet radiation sources located over an entire surface area of the housing.

16. The system of claim 13, wherein the door handle comprises a lever latch handle, wherein the enclosure comprises a bi-level enclosure including a first enclosure level located above the lever latch handle and a second enclosure level located underneath the lever latch handle, the first enclosure level and the second enclosure level each including an ultraviolet radiation source to irradiate the lever latch handle.

17. The system of claim 16, wherein the lever latch handle is rotatable from a horizontal position that is configured for opening and closing the door to a vertical position that is configured for receiving a treatment without having a capability to open and close the door, wherein the lever latch handle is outside an irradiation coverage range of the first enclosure level and the second enclosure level in the horizontal position, and the lever latch handle is inside the irradiation coverage range of the first enclosure level and the second enclosure level in the vertical position.

18. The system of claim 17, wherein the lever latch handle comprises a first set of handles and a second set of handles, both the first and second sets of handles including opposingly disposed handles each adapted for placement on a front side of the door and a back side of the door, the first set of handles positioned in the horizontal position and the second set of handles positioned in the vertical position, both the first and second sets of handles being rotatable between the horizontal position and the vertical position, wherein the door always includes one of the first set of handles and the second set of handles for opening and closing the door in the horizontal position and the other set of handles in the vertical position ready to receive a treatment, wherein the set of handles in the vertical position is configured for rotation to the horizontal position after treatment for opening and closing the door, permitting the set of handles in the horizontal position to move to the vertical position to receive a treatment.

19. The system of claim 13, wherein the disinfection illuminator further comprises at least one optical element configured to direct the ultraviolet radiation generated from the at least one ultraviolet radiation source to the door handle.

20. The system of claim 13, wherein the control unit of the disinfection illuminator further comprises an input component that permits an operator to adjust at least one of the plurality of operating parameters, and an output component that generates status information of the disinfection treatment to a user.

* * * * *